US007615548B2

(12) United States Patent
Gottlieb et al.

(10) Patent No.: US 7,615,548 B2
(45) Date of Patent: Nov. 10, 2009

(54) METHOD TO INHIBIT ISCHEMIA AND REPERFUSION INJURY

(75) Inventors: Roberta Gottlieb, Rancho Sante Fe, CA (US); Paul Wentworth, San Diego, CA (US); Eric F. Johnson, Encinitas, CA (US); Mark J. Yeager, Del Mar, CA (US); David Granville, Coquitlam (CA)

(73) Assignee: Radical Therapeutix, San Diego, CA (US)

( * ) Notice: Subject to any disclaimer, the term of this patent is extended or adjusted under 35 U.S.C. 154(b) by 144 days.

(21) Appl. No.: 11/030,717

(22) Filed: Jan. 6, 2005

(65) Prior Publication Data

US 2005/0215533 A1    Sep. 29, 2005

Related U.S. Application Data

(63) Continuation of application No. PCT/US2003/021536, filed on Jul. 9, 2003.

(60) Provisional application No. 60/394,642, filed on Jul. 9, 2002.

(51) Int. Cl.
*C11D 7/26*      (2006.01)
*C11D 3/00*      (2006.01)

(52) U.S. Cl. ...................... 514/183; 514/359

(58) Field of Classification Search .................. 514/221, 514/183, 359
See application file for complete search history.

(56) References Cited

U.S. PATENT DOCUMENTS

2005/0153871  A1   7/2005   Roman et al.

FOREIGN PATENT DOCUMENTS

WO    WO 01/151614    *   7/2001

OTHER PUBLICATIONS

Ha-Duon, N-T., et al. Arch. Biochem. Biophys. 2001, 394, 189-200.*
van Domburg et al. (van Domburg, R. T., et al. Drugs 2000, 60, 293-305.*
Grinyo, J. M. Transplantation Proceedings 2001, 33, 3741-3742.*
Fan et al. (J Mol Med 1999, 577-596).*
Mancy et al. (Biochemistry, 1996, 35, 16205-212).*
Nithipatikom et al. (Analytical Biochem, 292, 115-124, 2001).*
Zhu et al. (Jap J of Pharmacology, Feb. 2002).*
Adachi, N., et al., "Histaminergic H2 Blockade Facilitates Ischemic Release of Dopamine in Gerbil Striatum", *Brain Research*, 926, No. 1-2, XP002262423, ISSN: 0006-8993,(Feb. 1, 2002),172-175.
Brzozowski, T., et al., "Role of Gastric Acid Secretion in Progression of Acute Gastric Erosions Induced by Ischemia-Reperfusion into Gastric Ulcers", *European Journal of Pharmacology*, 398 No. 1, XP002262421, ISSN: 0014-2999,(Jun. 9, 2000),147-158.
Bysani, G. K., et al., "Role of Cytochrome P-450 in Reperfusion Injury of the Rabbit Lung", *Journal of Clinical Investigation*, 86, No. 5, XP009020936, ISSN: 0021-3738,(Nov. 1990),1434-1441.
Cordeiro, P. G., et al., "Prevention of Ischemia-Reperfusion Injury in a Rat Skin Flap Model: The Role of Mast Cells, Cromolyn Sodium, And Histamine Receptor Blockade", *Plastic And Reconstructive Surgery*, 105, No. 2, XP006021591, ISSN: 0032-1052,(Feb. 2000),654-659.
Kitano, M., et al., "Effects of Cimetidine on Acute Gastric Mucosal Injury Induced by Ischemia-Reperfusion in Rats", *Pharmacology (Basel)*, 55, No. 3, XP009021557, ISSN: 0031-7012,(1997),154-164.
Nakamoto, K., et al., "The Role of Endogenous Acid in the Development of Acute Gastric Ulcer Induced by Ischemia-Reperfusion in the Rat", *Life Sciences*, 62, No. 4, XP002262420, ISSN: 0024-3205,(1998),PL65, PL67.
Okajima, K., et al., "Ranitidine Reduces Ischemia/Reperfusion-Induced Liver Injury in Rats by Inhibiting Neutrophil Activation", *Journal of Pharmacology and Experimental Therapeutics*, 301,No. 3, XP002262422, ISSN: 0022-3565,(Jun. 2002),1157-1165.
Paller, M. S., et al., "Cytochrome P-450 mediates tissue-damaging hydroxyl radical formation during reoxygenation of the kidney", *Proceedings of the National Academy of Sciences*, 91, No. 15, XP001156148, ISSN: 0027-8424,(Jul. 1994),7002-7006.
Schneeberger, S., et al., "Protease Inhibitors as a Potential Target In Modulation of Postischemic Inflammation", *Drug News and Perspectives 2002 Spain*, 15 No. 9, XP009021572, ISSN: 0214-0934,(2002),568-574.
Tosaki, A., et al., "Treatment With Ranitidine of Ischemic Brain Edema", *European Journal of Pharmacology*, 264, No. 3, XP009021592, ISSN: 0014-2999,(1994),455-458.
Wu, S., et al., "Effect of Cimetidine on Isolated Rat Myocardial Reperfusion Injury", *Acta Pharmacologica Sinica*, 13 No. 1, XP009021590, ISSN: 0253-9756,(Jan. 1992),13-16.
Kim et al., "Selective degradation of mitochondria by mitophagy", Archives of Biochemistry and Biophysics 462 (2007), 245-253.
Bolli et al., "Myocardial Protection at a Crossroads—The Need for Translation Into Clinical Therapy", Circ Res.(2004), 125-134.
He, Huaping et al. Phosphorylation of Mitochondrial Elongation Factor Tu in Ischemic Myocardium—Basis for Chloramphenicol-Mediated Cardioprotection: Circulation Research, Grune and Stratton, Maltimore, US, vol. 89, No. 5, Aug. 31, 2001, pp. 461-467.
Clark, Wayne M. et al. "Reduction of Central Nervous System Reperfusion Injury in Rabbits Using doxycycline Treatment" Stroke, Lippincott Williams & Wilkins, US, vol. 25, No. 7, Jan. 1, 1994, pp. 1411-1415.
Lang-Lazdunski, Loïc et al. "The effects of FK506 on Neurologic and Histopathologic Outcome After Transient Spinal Cord Ischemia Induced by Aortic Cross-Clamping in Rats".
Htun Patrik et al. "Stimulation of Stress Activated Protein Kinases by Anisomycin Protects Ischemic Myocardium" Circulation, American Heart Association, Dallas, Tx, vol. 96, No. 8 Oct. 21, 1998, p. 252.
Bettini E. et al. "SAPK/JNK Activation in Rat Brain by Anisomycin: Possible Neuroprotective Role in Cerebral Ischemia" Abstracts of the Society for Neuroscience, Society for Neurosciences, Washington, DC, US, vol. 22, No. 1/03, Jan. 1, 1996.

(Continued)

*Primary Examiner*—Sreeni Padmanabhan
*Assistant Examiner*—Umamaheswari Ramachandran
(74) *Attorney, Agent, or Firm*—Knobbe, Martens, Olson & Bear LLP

(57) ABSTRACT

Methods of treating or inhibiting ischemia and reperfusion injury are provided.

6 Claims, 9 Drawing Sheets

OTHER PUBLICATIONS

Ikeda Yasuhiko et al. "PR-39, a Proline/Arinine-Rich Antimicrobial Peptide, Exerts Cardioprotective Effects in Myocardial Ischemia-Reperfusion" Cardiovascular Research, vol. 49, No. 1, Jan. 2001 pp. 69-77.

Kaji M. et al. "Effects of Long-Term Preoperative Administration of Low-Dose Erythromycin on Warm Ischemia-Reperfusion Pulmonary Injury" Database Medline [Online] US National Library of Medicine (NLM) Bethesda, MD, US; Nov. 1998 abstract.

Feeley Brian et al. "Sulfasalazine Inhibits Reperfusion Injury and Prolongs Allograft Survival in Rat Cardiac Transplants" Journal of Heart and Lung Transplantation, vol. 18, No. 11, Nov. 1999 pp. 1088-1095.

Casavilla F. et al. "Early Clinical and Histologic Viability of Human Liver-Small Intestinal Allografts After Implantation" Clinical transplantation 1994 DK, vol. 8, No. 1, 1994, pp. 49-53.

Halpert James R. et al. "Selective Inhibitors of Cytochromes P450" Toxicology and Applied Pharmacology, vol. 125, No. 2, 1994, pp. 163-175.

Wada K. et al. "A New Gastric Ulcer Model Induced by Ischemia-Reperfusion in the Rat: Role of Leukocytes on Ulceration in Rat Stomach" Life Sciences, Pergamon Press, Oxford, GB, vol. 59, No. 19, Jan. 1, 1996 pp. PL295-PL301.

Fukushima T. "Restorative Effects of Proton Pump Inhibitor, Omeprazole From Impaired Contractility of Ischemic Heart" Database Embase [Online] Elsevier Science Publishers, Amsterdam. NL; Mar. 1997.

Lewis David F.V. et al. "Molecular Modelling and Quantitative Structure-Activity Relationship Studies on the Interaction of Omeprazole With Cytochrome P450 Isozymes" Toxicology, Limerick, Ir, vol. 125, Sep. 29, 1998, pp. 31-44.

* cited by examiner

METHOD TO INHIBIT ISCHEMIA AND REPERFUSION INJURY

CROSS-REFERENCE TO RELATED APPLICATIONS

This application is a continuation under 35 U.S.C. § 111(a) of International Application No. PCT/US2003/021536 filed on Jul. 9, 2003 and published in English as WO 2004/004702 A2 on Jan. 15, 2004, which claims the benefit under 35 U.S.C. § 119(e) of the filing date of U.S. provisional application Ser. No. 60/394,642, filed on Jul. 9, 2002, the disclosures of which applications and publication are incorporated by reference herein.

STATEMENT OF GOVERNMENT RIGHTS

The invention was made, at least in part, with a grant from the Government of the United States of America (grants HL61518 and HL60590 from the National Institutes of Health). The Government may have certain rights to the invention.

BACKGROUND OF THE INVENTION

Ischemic heart disease is a leading cause of death in North America and is predicted to become more prevalent as the population ages (Scroggins, 2001). Ischemia and reperfusion lead to myocardial injury through a variety of mechanisms. For example, ischemia and reperfusion profoundly affect mitochondria, and preservation of their integrity and function is critical to salvage (Borutaite et al., 1995; DiLisa et al., 1998; Kay et al., 1997; Ferrari et al., 1996; Kobara et al., 1996). Oxidative phosphorylation is transiently increased after reperfusion but then diminishes; pyridine nucleotides are lost from the mitochondria, and respiration through complex I is impaired; superoxide production is increased, possibly through retrograde electron flow through complex I; the permeability transition pore opens, associated with loss of calcium homeostasis; and cytochrome c is released (Borutaite et al., 1995; Duan et al., 1989; DiLisa et al., 1998; Piper et al., 1985; Becker et al., 1999; Halestrap et al., 1998). However, it is not clear whether these mitochondrial alterations are initiated by an intrinsic response to the low oxygen tension of ischemia or arise in part due to changes in the cytosol. Cytosolic alterations are known to include acidosis, increased inorganic phosphate, elevated calcium, and a rise in long-chain acyl coenzyme A.

In addition, a variety of signal transduction pathways, including that of MAP kinases, particularly c-Jun $NH_2$-terminal kinase (JNK), and p38, are activated during myocardial ischemia and reperfusion. Previously it was shown that JNK translocates from cytosol to mitochondria in response to ischemia/reperfusion, and that in a model of metabolic inhibition in adult rabbit cardiomyocytes, inhibition of JNK is protective (He et al., 1999).

Ischemic preconditioning confers myocardial protection through a brief period of ischemia and reperfusion preceding the more sustained ischemia/reperfusion insult (Murry et al., 1986). Preconditioning is characterized by earlier recovery of mitochondrial function with more efficient resynthesis of ATP. Thus, it is clear from these diverse studies that ischemia and reperfusion activate cytosolic signals that target the mitochondria to modulate their response during ischemia and reperfusion, and furthermore, that preconditioning also involves signaling from cytosol to mitochondria.

Current therapies for ischemic heart disease are directed at the restoration of blood flow to the ischemic region. However, during reperfusion the heart undergoes further damage due in large part to the generation of reactive oxygen species (ROS), e.g., superoxide anion (Singh et al., 1995; Flaherty et al., 1988). Elevated ROS can be detected within minutes after the reintroduction of oxygen to ischemic tissues (Bolli et al., 1995). ROS have been shown to be key mediators of cellular and myocardial injury, with free radical scavengers attenuating the associated injury (Cesselli et al., 2001). Low levels of superoxide play a role in signaling pathways possibly contributing to preconditioning (Sun et al., 1996) and the development of hypertrophy (Ito et al., 1995). However, higher levels are detrimental, causing lipid peroxidation and apoptosis (Siwik et al., 1999; Halmosi et al., 2001). There are no current therapies for reperfusion injury.

Thus, what is needed is a method to inhibit ischemia and/or reperfusion injury.

SUMMARY OF THE INVENTION

The invention provides a method to inhibit, treat or prevent injury associated with ischemia and/or reperfusion in a mammal, e.g., a human. Ischemia and/or reperfusion injury are associated with myocardial ischemia (resulting from, for example, acute myocardial infarction, elective angioplasty, coronary artery bypass graft, surgery involving cardiac bypass or cardiac transplantation), cerebral ischemia (resulting from, for example, stroke, head trauma or drowning), intestinal ischemia, renal ischemia or tissue ischemia (resulting from sepsis, cardiac arrest, drowning or shock).

The method involves administering to a mammal having or at risk of injury associated with ischemia and/or reperfusion an effective amount of one or more agents. These agents include but are not limited to $H_2$-receptor antagonists; $H^+/K^+$ ATPase inhibitors; antimicrobials; antifugals, e.g., azoles, central nervous system (CNS)-active agents including tricyclic antidepressants, serotonin reuptake inhibitor antidepressants, phenothiazine antipsychotics, and benzodiazepines anxiolytics; nonsteroidal anti-inflammatory drugs (NSAIDs); metyrapone; 7-ethoxyresorufin; HMG-CoA synthase inhibitors; sartans, and calcium channel blockers; preferably the agent inhibits the amount or activity of one or more cytochrome P450 (CYP450 or CYP) enzymes. In one embodiment, the agent is a $H_2$-receptor antagonist, e.g., cimetidine, ranitidine or ebrotidine. In one embodiment, the agent is a H+/K+-ATPase inhibitor, e.g., omeprazole. In one embodiment, the agent is an antimicrobial or an antifungal, for instance, chloramphenicol, ketoconazole, sulfaphenazole, clotrimazole or miconazole. In one embodiment, the agent is a tricyclic antidepressant, e.g., clomipramine, amitriptyline or desipramine. In one embodiment, the agent is a serotonin reuptake inhibitor, for instance, fluoxetine, sertraline or paroxetine. In another embodiment, the agent is a phenothiazine, e.g., chlorpromazine. In one embodiment, the agent is a benzodiazepine, e.g., flurazepam. In another embodiment, the agent is a nonsteroidal anti-inflammatory agent, e.g., diclofenac, flufenamine, fenoprofen, flubiprofen or ketoprofen. In another embodiment, the agent is a calcium channel blocker. Exemplary preferred agents include but are not limited to the $H_2$-receptor antagonists cimetidine, ranitidine, and ebrotidine; the $H^+/K^+$ ATPase inhibitor omeprazole; antimicrobials and antifungals such as chloramphenicol, econazole, ketoconazole, sulfaphenazole, trimethoprim, sulfamethoxazole, clotrimazole, and miconazole; CNS-active agents including tricyclic antidepressants such as clomipramine, amitriptyline, and desipramine, serotonin reuptake inhibitor antidepressants such as fluoxetine, sertraline, and paroxetine, phenothiazine antipsychotics such as chlorpromazine; benzodiazepines anxiolytics such as flurazepam and medazapam; NSAIDs such as diclofenac, flufenamine, fenoprofen, flurbiprofen, and ketoprofen; metyrapone; 7-ethoxyresorufin; HMG-CoA synthase inhibitors such as the statins; and calcium channel blockers such as diltiazem, verapamil, lercanidipine, nifedipine, nisoldipine, nicardipine, isradipine, nitrendipine, felodipine, and amlodipine, agents which inhibit one or more cytochrome P450 enzymes. Another effective agent may be the antiarrhythmic amiodarone. Additional agents useful to treat the indications or conditions described herein are flavonoids such as resveratrol and other related compounds present in red wine, grape seed extracts, green tea, and other dietary and herbal sources of flavonoids. The administration of the one or more agents may be prior to ischemia, after the onset of ischemia, after the onset of reperfusion, or any combination thereof. In one embodiment, the one or more agents may be administered intravenously. In one embodiment, the one or more agents may be orally administered. In one embodiment, the one or more agents are administered via a catheter, for instance, an angioplasty catheter, to a coronary artery. In one embodiment, the one or more agents are administered via a catheter which comprises a drug delivery balloon.

It is also envisioned that agents other than those described above may be employed in the methods of the invention, for instance, alone or in addition to the agents described above, agents including, but not limited to, agents that inhibit mitochondrial superoxide production, e.g., complex I inhibitors such as idebenone, rotenone, p-hydroxy-mercuribenzoate, rolliniastatin-2, capsaicin and amytal; complex III inhibitors, e.g., myxothiazol, antimycin A and mucidin (strobilurin A); and agents that inhibit superoxide production at other sites, for instance, xanthine oxidase inhibitors (e.g., allopurinol), and NAD(P)H oxidase inhibitors (e.g., apocynin and diphenyleneiodonium).

As described herein, pretreatment of hearts with chloramphenicol, an inhibitor of cytochrome P450, prior to ischemia and reperfusion, significantly reduced infarct size (by about 90%). Further, chloramphenicol administered after the ischemic insult reduced the size of the infarct by about 60 to about 80%. This was surprising as most agents that are cardioprotective when administered before ischemia, are not necessarily cardioprotective when administered after the onset of ischemia. Chloramphenicol also inhibits cytochrome P450 enzymes. As further described herein, cimetidine and sulfaphenazole, both of which inhibit cytochrome P450 enzymes but not protein synthesis, were shown to prevent or reduce reperfusion injury and $O_2^{*-}$ generation in the heart. Interestingly, while weak inhibition of more than one isozyme may occur at the concentrations of inhibitors that were tested, the cytochrome P450 2C family is the only family of P450 isozymes that is known to be inhibited by chloramphenicol, sulfaphenazole, and cimetidine. Moreover, superoxide production, which more than doubles after ischemia and reperfusion, was reduced by 75% by drug treatment. These compounds can also enhance coronary blood flow after ischemia, e.g., by improving the vasodilatory effects of nitric oxide owing to diminished superoxide production, and enhance cardiac contractility after ischemia/reperfusion, e.g., by preventing the production of the cardiotoxic cytochrome P450 metabolite 14,15-epoxyeicosatrienoic acid (14,15-EET).

Thus, agents which inhibit one or more cytochrome P450 enzymes, for instance, one or more members of the cytochrome P450 1A family, e.g., 1A1, one or more members of the cytochrome P450 1B family, e.g., 1B1, one or more members of the cytochrome P450 2B family, e.g., 2B6 or 2B7, one or more members of the cytochrome P450 2C family, e.g., 2C8-19, one or more members of the cytochrome P450 2D family, e.g., 2D6, one or more members of the cytochrome P450 2E family, e.g., 2E1, one or more members of the cytochrome P450 2F family, e.g., 2F2, one or more members of the cytochrome P450 4A family, e.g., 4A10, one or more members of the cytochrome P450 2J family, e.g., 2J2, or one or more members of the cytochrome P450 4B family, e.g., 4B1, can limit the production of cardiotoxic agents including singlet oxygen, superoxide and eicosanoids, are cardioprotective and so abrogate injury due to ischemia and reperfusion that is associated with a variety of indications or conditions, for instance, myocardial infarction. Moreover, since these agents can be administered with the onset of reperfusion, they are clinically applicable as an adjuvant to angioplasty, e.g., which includes stent placement, or thrombolytic therapy.

Accordingly, the agents described herein including inhibitors of one or more cytochrome P450 enzymes have value for the treatment of the following exemplary indications or conditions: acute myocardial infarction; angioplasty; coronary artery bypass graft surgery; surgery involving cardiac bypass; ischemia/reperfusion injury in any organ; stroke (cerebrovascular accident); organ transplantation; septic or traumatic shock, as well as other pathologic processes, including atherosclerosis, hypertension, cocaine-induced heart disease, smoking-induced heart disease, heart failure, and pulmonary hypertension.

In one embodiment of the invention, a method to treat or inhibit ischemia and/or reperfusion injury is provided. The method involves administering to a mammal, for instance, a human, having or at risk of ischemia and/or reperfusion injury an effective amount of one or more agents including $H_2$-receptor antagonists; $H^+/K^+$ ATPase inhibitors; antimicrobials; antifungals; central nervous system (CNS)-active agents including tricyclic antidepressants, serotonin reuptake inhibitor antidepressants; phenothiazine antipsychotics; benzodiazepines anxiolytics; nonsteroidal anti-inflammatory drugs (NSAIDs); metyrapone; 7-ethoxyresorufm; HMG-CoA synthase inhibitors; sartans; or calcium channel blockers inhibitors, which agent(s) preferably inhibit one or more cytochrome P450 enzymes. The administration of the one or more agents may be prior to ischemia, after the onset of ischemia, after the onset of reperfusion, or any combination thereof.

In one aspect of the invention, the method involves administering to a mammal, such as a human, prior to the onset of ischemia, an amount of one or more agents including $H_2$-receptor antagonists; $H^+/K^+$ ATPase inhibitors; antimicrobials; antifungals; central nervous system (CNS)-active agents including tricyclic antidepressants, serotonin reuptake inhibitor antidepressants; phenothiazine antipsychotics; benzodiazepines anxiolytics; nonsteroidal anti-inflammatory drugs (NSAIDs); metyrapone; 7-ethoxyresorufm; HMG-CoA synthase inhibitors; sartans; or calcium channel blockers inhibitors, which agent(s) preferably inhibit one or more cytochrome P450 enzymes, effective to treat or inhibit ischemia and/or reperfusion injury, e.g., due to a vascular interventional procedure. The administration may begin prior to ischemia and/or reperfusion and may continue after the onset of ischemia and/or reperfusion. Agents including inhibitors of cytochrome P450 enzymes may thus be employed as a prophylactic treatment before angioplasty, coronary artery bypass graft or other vascular interventional procedures, or as a pretreatment for donor organs, e.g., a heart, lung, liver or kidney, in the transplant setting, e.g., before organ harvest and optionally administered to the organ recipient, as well as to protect the heart against ischemic injury such as occurs in the setting of acute angina.

Accordingly, the invention provides a method to inhibit ischemia and reperfusion injury in a mammalian donor organ. The method involves contacting the donor organ with an effective amount one or more agents selected from the group consisting of a $H_2$-receptor antagonist, a H+/K+-ATPase inhibitor, an antimicrobial, an antifungal, a tricyclic antidepressant, a serotonin reuptake inhibitor, a phenothiazine, a benzodiazepine, a calcium channel blocker, and a nonsteroidal anti-inflammatory drug, wherein the one or more agents inhibit one or more cytochrome P450 enzymes. In one embodiment, the agent is a $H_2$-receptor antagonist, e.g., cimetidine, ranitidine or ebrotidine. In one embodiment, the agent is a H+/K+-ATPase inhibitor, e.g., omeprazole. In one embodiment, the agent is an antimicrobial or an antifungal, for instance, chloramphenicol, ketoconazole, sulfaphenazole, clotrimazole or miconazole. In one embodiment, the agent is a tricyclic antidepressant, e.g., clomipramine, amitriptyline or desipramine. In one embodiment, the agent is a serotonin reuptake inhibitor, for instance, fluoxetine, sertraine or paroxetine. In another embodiment, the agent is a phenothiazine, e.g., chlorpromazine. In one embodiment, the agent is a benzodiazepine, e.g., flurazepam. In another embodiment, the agent is a nonsteroidal anti-inflammatory agent, e.g., diclofenac, flufenamine, fenoprofen, flubiprofen or ketaprofen. In another embodiment, the agent is a calcium channel blocker.

In another embodiment, the invention provides a method to inhibit reperfusion injury by administering to a mammal, after the onset of ischemia, an effective amount of one or more of the agents described herein, e.g., an agent that inhibits one or more cytochrome P450 enzymes.

The agents of the invention may be administered by any route or means, including, but not limited to, by administration of agent intravenously (e.g., before a scheduled procedure), by catheter to an organ at risk of ischemic or reperfusion injury (e.g., intracoronary delivery via an angioplasty catheter with a drug delivery balloon), or orally, or in combination with thrombolytic agents (i.v.).

The present invention also provides a composition and kit which includes a substantially pure preparation of one or more of the agents described herein as useful to inhibit, prevent or treat ischemic or reperfusion injury. The composition is composed of an agent in an amount effective to selectively inhibit one or more cytochrome P450 enzymes and a carrier such as a pharmaceutically acceptable carrier. The composition or kit optionally includes one or more other therapeutic agents, e.g., an agent of the invention and a thrombolytic. The kit may be composed of two or more containing means, for example, two vials each with a different agent, or a single containing means with one or more of the agents described herein.

DETAILED DESCRIPTION OF THE INVENTION

I. Definitions

Figure 1A:
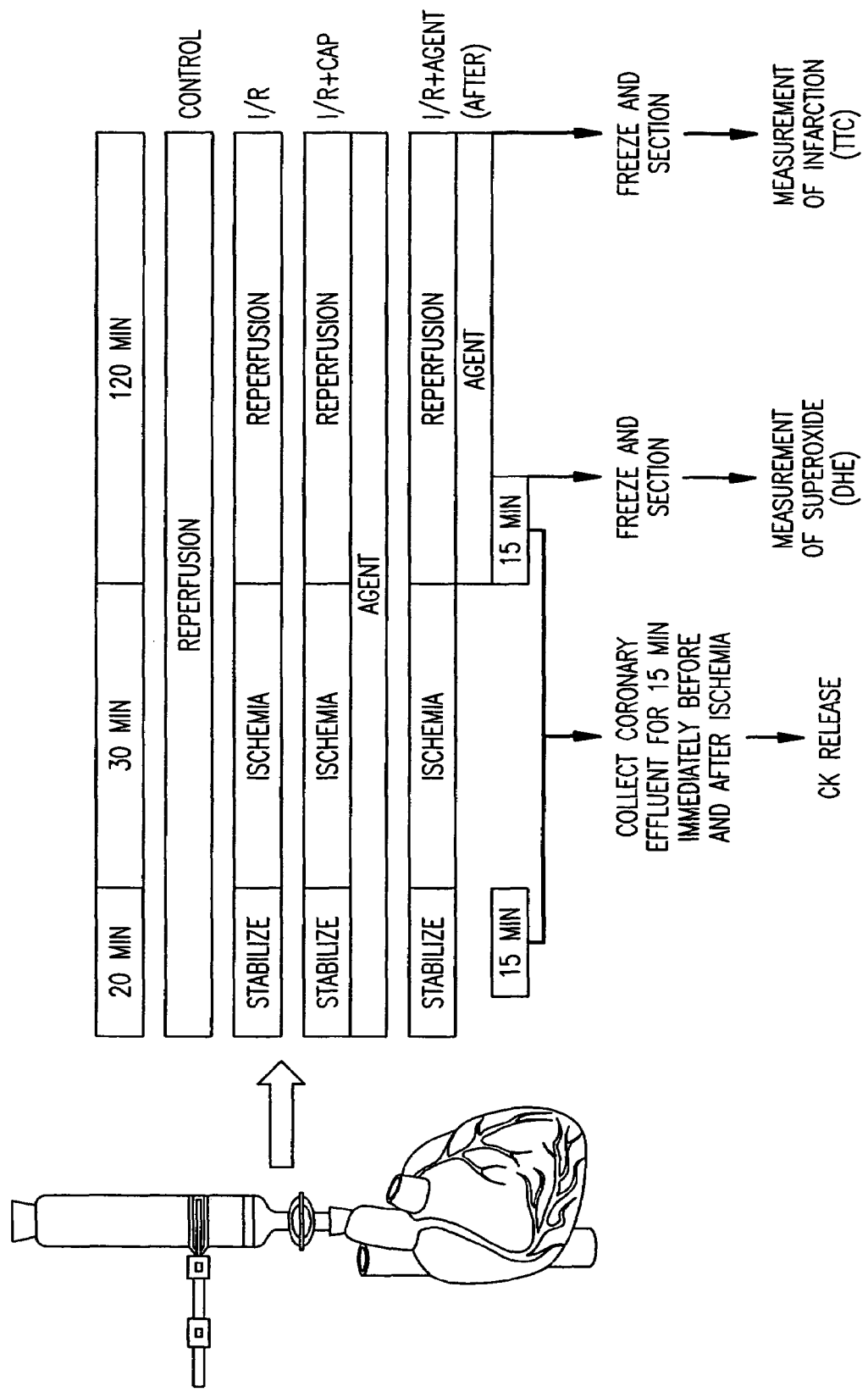
FIG. 1. Experimental protocol for treatment of isolated hearts (A) or rabbits (B) during ischemia and reperfusion or reperfusion only.
Figure 1B:
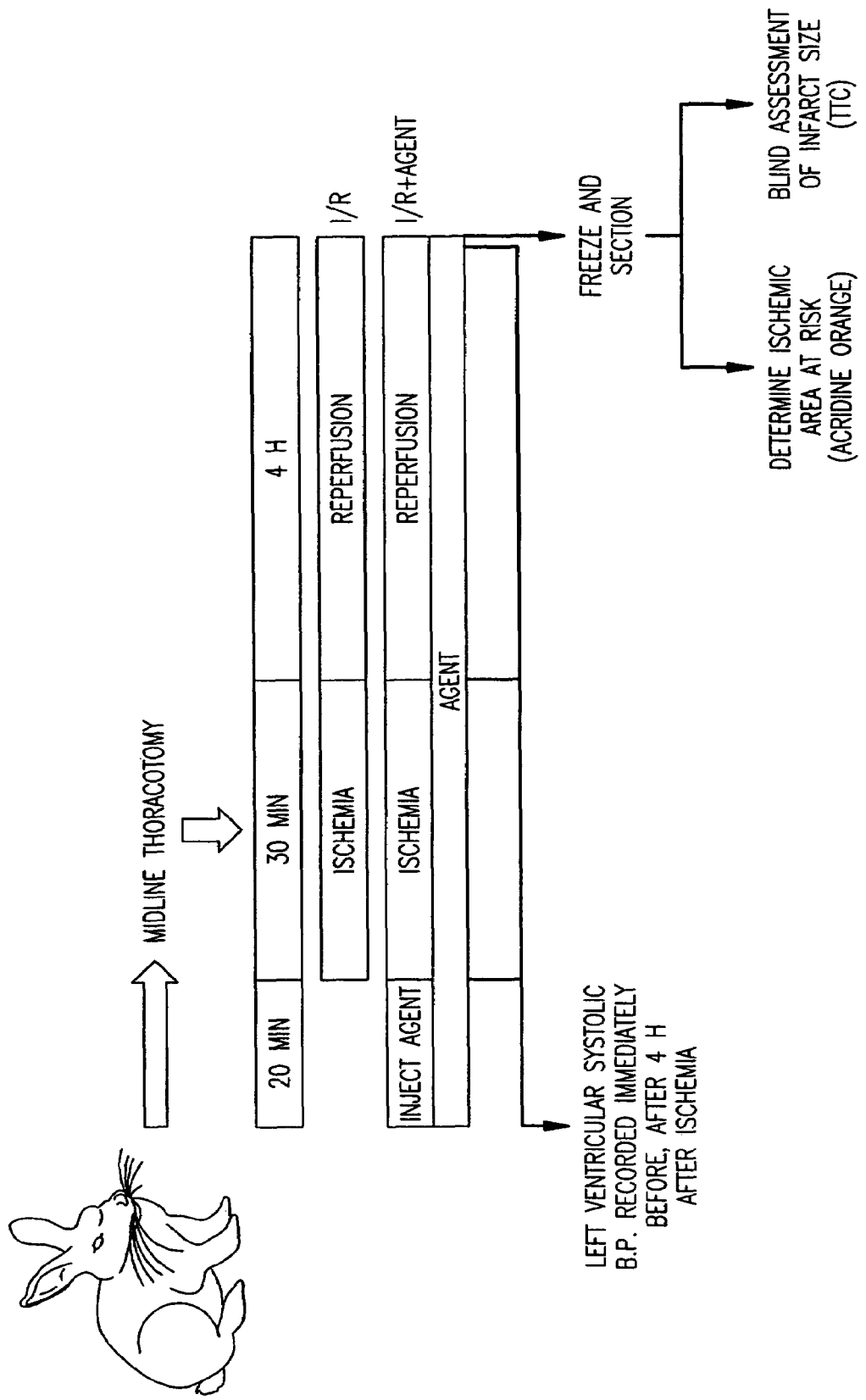

The term "an effective amount" of an agent is the amount sufficient to treat, inhibit, or prevent ischemia and/or reperfusion injury associated with indications and conditions including, but not limited to, myocardial infarction, stroke, septic shock, traumatic shock, and associated with vascular interventional procedures including angioplasty, any surgery involving cardiac bypass, cardiac artery bypass graft surgery and organ transplantation. A preferred effective amount is that which selectively inhibits one or more cytochrome P450 enzymes. For instance, in vitro, 10 µM sulfaphenazole is selective for inhibition of cytochrome P450 2C. Exemplary amounts for exemplary agents for selective inhibition in vivo are 50 mg/kg/day chloramphenicol; 800 to 1600 mg/day, optionally in divided doses, or 50 mg/hr (infusion) for cimetidine; 80 to 200 mg/day (divided doses) or 160 mg/hr (infusion) for trimethoprim; 800 to 1600 mg/day (divided doses) for sulfamethoxazole; and 750 mg every four hours (15 mg/kg =single dose) for methyrpone. Methods to identify amounts which selectively inhibit cytochrome P450 enzymes are known to the art (see, e.g., Masimirembwa et al., 2001; Kelly et al., 2000; Masubuchi et al., 1998). An effective amount of an agent useful in the methods of the invention can vary according to factors such as the agent selected, and the age, sex, health and weight of the mammal, and can be determined by methods within the skill of the art.

By "pharmaceutically acceptable" it is meant a carrier, diluent, excipient, and/or salt that is compatible with the other ingredients of the formulation, and not deleterious to the recipient thereof.

"Pharmaceutically acceptable salts" are salts of compounds employed in this invention which are sufficiently acidic or basic to form non-toxic acid or base salts, e.g., prepared by reacting a free acid with a suitable organic or inorganic base. Examples of salt forms may include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, triethiodide, and valerate, and salts derived from inorganic bases including aluminum, ammonium, calcium, copper, ferric, ferrous, lithium, magnesium, manganic salts, manganous, potassium, sodium, zinc, and the like. Salts derived from organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Salts derived from carboxylic acids include esters thereof, preferably alkyl esters.

Pharmaceutically acceptable salts may be obtained using standard procedures well known in the art, for example, by reacting a sufficiently basic compound such as an amine with a suitable acid affording a physiological acceptable anion.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, about 90%, about 95%, and about 99%. Most preferably, the object species is purified to essential homogeneity (contaminant species cannot be detected in the composition by conventional detection methods) wherein the composition consists essentially of a single macromolecular species.

A "mammal" as used herein includes humans, dogs, cats, mice, rats, rabbits and livestock, for example, buffalo, horses, cattle, sheep, goats, pigs and the like. "Preconditioning" includes a brief period of cellular stress that confers resistance to a second, more severe stress.

II. Exemplary Agents and Methods to Identify Agents Useful in the Methods of the Invention The agents of the invention are useful to treat a mammal having (afflicted with) or at risk of having ischemia and/or reperfusion injury. As inhibitors of cytochrome P450 enzymes were found to be useful to inhibit ischemia and/or reperfusion injury to myocardium, these agents, as well as others disclosed herein, may be useful to treat or prevent a wide range of indications or conditions associated with ischemia and/or reperfusion injury. For example, these agents include, but are not limited to, $H_2$-receptor antagonists, H+/K+ATPase inhibitors, antimicrobials and antifungals, active agents including tricyclic antidepressants, serotonin reuptake inhibitor antidepressants, phenothiazine antipsychotics and benzodiazepines anxiolytic. Preferred agents include $H_2$-receptor antagonists, e.g., cimetidine, ranitidine, and ebrotidine; $H^+/K^+$ ATPase inhibitors, e.g., omeprazole; antimicrobials and antifungals, e.g., chloramphenicol, econazole, ketoconazole, sulfaphenazole, trimethoprim, sulfamethoxazole, clotrimazole, and miconazole; central nervous system (CNS)-active agents including tricyclic antidepressants such as clomipramine, amitriptyline, and desipramine, serotonin reuptake inhibitor antidepressants such as fluoxetine, sertraline, and paroxetine, phenothiazine antipsychotics, e.g., chlorpromazine, and benzodiazepines anxiolytics, for instance, flurazepam and medazapam; non-steroidal anti-inflammatory drugs (NSAIDs), e.g., diclofenac, flufenamine, fenoprofen, flurbiprofen, and ketoprofen; metyrapone; 7-ethoxyresorufin; HMG-CoA synthase inhibitors, e.g., statins; sartans, and calcium channel blockers, e.g., diltiazem, verapamil, lercanidipine, nifedipine, nisoldipine, nicardipine, isradipine, nitrendipine, felodipine, and amlodipine. As described herein, the use of inhibitors with specificity for certain cytochrome P450 enzymes rather than the use of broad spectrum inhibitors, and/or specific doses of cytochrome P450 inhibitors which selectively inhibit more or more cytochrome P450 enzymes, may minimize side effects resulting from disrupting unrelated physiological processes.

A. Exemplary Methods to Identify Agents

Methods to identify agents useful in the methods of the invention include in vitro and in vivo methods. In vitro methods can employ tissue cultures or isolated organs or tissues. For instance, renal epithelial cells can be cultured in vitro. To simulate ischemia, after formation of a confluent epithelial cell sheet, the cells are washed with phosphate buffered saline, and the monolayer is immersed in mineral oil (Meldrum et al., 2002). Exposure to mineral oil restricts cell exposure to oxygen and nutrients, and prevents metabolite washout. Simulated ischemia can also be performed on other cell types in tissue culture, such as in isolated myocytes (Gottlieb et al., 1994; Gottlieb et al., 1996; Henry et al., 1996). To screen agents for use in inhibiting or preventing ischemia, the agents may be added to the cultures before or during ischemia. Then the amount of cellular injury in control cultures versus agent exposed cultures determined. For renal ischemia, in vitro determinations of creatine levels may be useful to identify agents that decrease renal ischemic injury (Brasile et al., 2002) while determinations of CK levels (e.g., using the CK EC 2.7.3.2 UV-Test kit, Sigma) may be useful to identify agents that decrease myocardial ischemic injury.

Other in vitro methods to identify efficacious agents for myocardial ischemia include the determination of CK release, superoxide production and coronary flow in isolated hearts exposed to a test agent. For instance, hearts are excised from an anesthetized mammal such as a rabbit and quickly cannulated onto a Langendorff perfusion apparatus. The heart is perfused with Krebs-Ringer buffer, e.g., for 15 to 60 minutes, before ischemia/reperfusion episodes. No-flow ischemia is maintained for a period of time, e.g., 5 to 60 minutes, and reperfusion is accomplished by restoring flow, e.g., for 5 to 60 minutes. Ischemic preconditioning can be induced by, for example, three 5 minute cycles of no-flow ischemia and reperfusion immediately preceding the regular ischemia and reperfusion. The agent to be tested may be added prior to ischemia induction, at the onset of ischemia, at the onset of reperfusion, or any combination thereof. CK release in control versus treated hearts may be measured using the CK EC 2.7.3.2 UV-Test kit (Sigma) per the manufacturer's instructions.

Similarly, isolated kidneys may be used to screen agents in a renal model of transplantation (see Brasile et al., 2002).

Superoxide production can be assessed via the conversion of dihydroethidium (DHE) to ethidium (Miller et al., 1998). Tissue, e.g., heart, slices (1 mm thick) are stained in 2 µM DHE (Molecular Probes, Eugene, Oreg.) in PBS in the dark at 37° C. for 20 minutes. Sections imaged on an ultraviolet transilluminator (Fisher Scientific) with a Kodak DC120 digital camera (Kodak) using Kodak Digital Science 1D software (Kodak) are saved as TIFF files and analyzed using Adobe Photoshop 5.5. The relative fluorescence intensity reflecting superoxide production was quantified as the ratio of fluorescent (white) pixels to the total heart area. Statistical analysis was performed between groups using ANOVA. Heart slices can also be used to detect the size of the infarcted region (see Examples).

Agents may also be tested for the ability to inhibit one or more cytochrome P450 enzymes in in vitro assays (see Example II).

The agents of the invention can be assayed for their effect in protecting against or inhibiting or treating reperfusion injury associated with myocardial, intestinal, renal, or cerebral ischemia in animal models. Myocardial infarction is the result of acute closure of a coronary vessel usually due to thrombosis secondary to rupture of an atherosclerotic plaque. The damage to the adjacent myocardium and resultant heart failure is secondary to the period of ischemia and the damage caused during the reperfusion period. Reperfusion injuries are associated with increased oxygen free radicals and inflammatory mediators. Exemplary animal models of myocardial ischemia are disclosed in Zhang et al., 1999; Ning et al., and the Examples herein.

Both rats and rabbits have been used as models for intestinal ischemia (Kuenzler et al., 2002; Caglayan et al., 2002). In a rabbit intestinal ischemia/reperfusion model, for instance, the animal undergoes laparotomy, and then an atraumatic microvascular clamp is placed across the mesenteric artery, allowing occlusion of the related vein (Caglayan et al., 2002). The marginal vessels at both ends of the segment are divided and ligated, and the intramural collateral blood flow is stopped with atraumatic intestinal clamps (Caglayan et al., 2002). Mesenteric ischemia is confirmed when the mesenteric pulsations are lost and the intestinal segment becomes pale. The bowel is then returned to the abdominal cavity and the incision is closed. After the desired ischemic period (e.g., 60 minutes), a relaparotomy is performed and the microvascular clamp on the artery is removed to allow reperfusion. Injury can be detected by blood levels of intracellular enzymes, e.g., aspartate aminotransferase, CK, and lactate dehydrogenase (Caglayan et al., 2002), or galactose or glycine absorption (Kuenzler et al., 2002). Also, intestinal mucosal lesions can be measured as described in Chin et al., 1970.

Likewise, renal ischemia can be induced in rodent models by clamping of one or both renal arteries, and reperfusion induced by removing the clamps (Yoshida et al., 2002; Miyazawa et al., 2002). Levels of creatine and neutrophil, intermediate T cell and/or polymorphonuclear lymphocytes in control animals and animals contacted with a test agent can then be determined (Brasile et al., 2002; Miyazawa et al., 2002). Cerebral ischemia can be induced transiently in the rat by, for instance, the method of middle cerebral artery occlusion (Loy et al., 2002; Longa et al., 1989).

A porcine model for sepsis associated with hepatic ischemia and reperfusion injury may be employed to screen agents (Lemaire et al., 1994). In this model, a portacaval shunt is created, and then liver ischemia is achieved by clamping the hepatic pedicle (i.e., the portal vein and the common hepatic artery). Reperfusion is achieved by closing the portacaval shunt. A rat model of chronic sepsis which employs cecal ligation and perforation, may also be employed (Scott et al., 2002).

Development of atherosclerosis is a complex process involving smooth muscle cells, endothelial cells and inflammatory cells, and, in particular, monocyte-derived tissue macrophages, B or T cells, and reactive oxygen species are believed to promote atherosclerosis. Once endothelial cells are activated, they express adhesion molecules important for the extravasation of inflammatory cells. The activated endothelial cells express, among other adhesion molecules, E-selectin, P-selectin, and ICAM-1, which in turn participate in the extravasation of leukocytes. Potent pro-inflammatory cytokines were also expressed at the sites of incipient vascular lesions. TNF-$\alpha$, IL-1, as well as several chemokines including IL-8 and MCP-1, have been detected at elevated levels in atherosclerotic lesions.

It is now well accepted that the acute stability of vascular lesions is a more important determinant of short-term, e.g., less than several years, risk of myocardial infarction, than is total plaque burden. Inhibitors of cytochrome P450 enzymes may be useful to inhibit or prevent atherosclerosis, e.g., by reducing plaque burden or lesion development, or increasing plaque stability, and thus reduce the risk of myocardial infarction. Animal models of atherosclerosis are known to the art and may be employed to screen for agents with desirable properties (see, e.g., Post et al., 2002; Berg et al., 2002; George et al., 2002; Nishimoto et al., 2002).

Hypertension is a risk factor for atherosclerosis. To determine whether an agent of the invention is useful to inhibit or treat hypertension, a rabbit model is employed. New Zealand white rabbits are fed an atherogenic diet for three weeks to induce plaque formation. One half of each group of rabbits is administered a test agent. Aortic coarctation is created in one group of the rabbits by wrapping a Dacron band around the midportion of the descending thoracic aorta (stenosis group). Another group of rabbits undergo the banding technique without aortic constriction. Yet another group of rabbits serve as controls.

To determine whether an agent is useful to inhibit ischemia or reperfusion injury associated with vascular interventional procedures, a number of animal models may be employed (see, e.g., Wilczek et al., 2002; Maffia et al., 2002; Yasuda et al., 2002; Kipshidze et al., 2002; Yoon et al., 2002).

B. Exemplary In Vitro Methods to Identify Cytochrome P450 Inhibitors Useful to Treat Cardiac Indications Cardiac tissue contains cardiomyocytes, which provide the mechanical force, consume most of the oxygen and energy of the heart, and contain most of the mitochondria in the heart. Cardiac tissue also contains endothelial cells, which line the capillaries of the heart, which cells produce nitric oxide and other factors that regulate vasomotor tone and cardiac contractility. Endothelial cells, while equal in number to cardiomyocytes in the heart, represent about 1/10 the mass of the heart.

Cytochrome P450 enzymes (EC 1.14.14.1, non-specific monooxygenases) are heme proteins that are defined by a characteristic absorption spectrum, where the Fe (II) CO complex has a characteristic Soret band near 450 nm due to axial ligation with a cysteine thiolate of the protein. The cytochrome P450 enzymes are membrane-bound, terminal oxidases that exist in a multi-enzyme system that also includes a FAD/FMN-containing NADPH-cytochrome P450 reductase and cytochrome $b_5$. Members of the cytochrome P450 enzyme superfamily oxidize, peroxidize and/or reduce cholesterol, steroids, arachidonic acid, bradykinin, vitamins, xenobiotics and numerous therapeutic substances in an oxygen- and NADPH-dependent manner. Some cytochrome P450 isoforms are specific in their choice of substrates but many, particularly those in the endoplasmic reticulum, catalyze a large number of reactions.

There are many different cytochrome P450 enzymes and there can be >30 cytochrome P450 genes expressing their products in a single organism, and many of these are concurrently produced in a single tissue. The cytochrome P450 genes are classified on the basis of their coding sequence and sequence homology (Nebert et al., 1991). Cytochrome P450 proteins from all species that possess 40% sequence identity or greater are included in the same family, which is designated by an Arabic number. Proteins that share greater than 55% homology are then grouped together in the same subclass as designated by a capital letter; the final number identifies specific gene products (Coon et al., 1992).

The vast majority of cytochrome P450 enzymes are expressed in the liver, with significantly lower levels being expressed in extra-hepatic tissues. However, some cytochrome P450 enzymes are predominantly detected in the heart, vasculature, gastrointestinal tract, kidney and lung (Oyekan et al., 2002; Scarborough et al., 1999).

Cytochrome P450 distribution differs between right and left ventricle, and also differs according to cell type. Cytochrome P450 monooxygenases are present in both cardiac endothelial cells and cardiomyocytes, and are important to the regulation of coronary flow, and production of reactive oxygen species (ROS), e.g., superoxide, and vasoactive eicosanoids. Eicosanoids in turn regulate intracellular signal transduction pathways, plasma membrane ion channels, and potentially the mitochondrial ATP-sensitive potassium channel (mito KATP) that is implicated in cardioprotection by preconditioning.

Inhibitors of cytochrome P450 enzymes may be selected based on their specificity, e.g., fluvastatin is a potent inhibitor of CYP2C9 (Scripture et al., 2001), while lovastatin, atorvastatin, simvastatin, and derivastatin inhibit CYP2C19 and CYP3A4, and atorvastatin, cerivastatin, and fluvastatin are moderate inhibitors of CYP2D6. To identify selective inhibitors of particular cytochrome P450 isozymes, as well as to identify cytochrome P450 isozymes that are responsible for reperfusion injury in heart tissue, for instance, those that metabolize arachidonic acid and linoleic acid, various assays including those described herein and/or assays with isozyme-specific substrates and/or inhibitors, may be employed. Cytochrome P450 isozymes are rather loosely coupled to the reductase. This inefficient coupling results in generation of the byproduct superoxide, which is produced to a greater extent by some isozymes than others. After hypoxia or exposure to oxidative stress (e.g., hydrogen peroxide), some cytochrome P450 isozymes become even further uncoupled and generate superoxide even more vigorously. It was observed that H9c2, a rat embryonic cell line, and neonatal rat cardiomyocyces, undergo apoptosis and produce superoxide in response to hydrogen peroxide, which can be rescued by treatment with a cytochrome P450 inhibitor such as sulfaphenazole. Those results suggested that hydrogen peroxide treatment uncouples cytochrome P450 isozymes, causing increased ROS production leading to apoptosis.

1. Endothelial Cells

Endothelial cells and cardiomyocytes are employed in assays to identify cytochrome P450 isozymes that are responsible for reperfusion injury in heart tissue, as the cytochrome P450 isozymes in endothelial cells may be different than those in cardiomyocytes. Thus, endothelial cells, such as human coronary artery endothelial cells (HAEC) and/or rat heart endothelial cells (obtained by collagenase perfusion and dissociation of the rat heart), and cardiomyocytes are screened for cytochrome P450 activity, particularly their ability to generate superoxide, and their susceptibility to cytochrome P450 inhibition, e.g., cardioprotective cytochrome P450 inhibitors. For example, HAECs, rat endothelial cells and/or adult cardiomyocytes are screened for the ability of a cytochrome P450 inhibitor to rescue those cells from $H_2O_2$-induced apoptosis. Apoptosis is scored by reduction of the tetrazolium dye, MTT, using a spectrophotometric plate reader. MTT is reduced to a colored product by dehydrogenases in living cells; therefore the MTT assay scores viable cells. Results are verified by fluorescence microscopy of live cells using Rhodamine 123 to stain mitochondria with normal membrane potential, and Hoechst 33432 to stain nuclei. Dihydroethidium is employed as a readout for superoxide production.

2. Isozyme Specific Inhibitors

HAECs are employed with Gentest substrates to detect specific human cytochrome P450 isozymes and the efficacy of various cytochrome P450 inhibitors. The specific isozymes known to be present in human heart tissue include those listed in Table 1. Substrates are commercially available for CYP 1A, 2B, 2C, 2D, 2E, and 4A isozymes. Arachidonic acid metabolites can be detected using LC-MS-MS. A close correlation between protective efficacy by a subset of cytochrome P450 inhibitors and the isozyme that is sensitive to the same subset of inhibitors implicates a particular isozyme as responsible for peroxide-induced injury. The same isozyme is also likely responsible for reperfusion injury in the heart.

TABLE 1

CYP isozymes in human heart.

| | Physiologic Activity |
|---|---|
| 1A1 | metabolism of tryptamine |
| 2B6/7 | arachidonic acid epoxidation |
| 2C8/19 | arachidonic acid epoxidation, phospholipid hydrolysis |
| 2D6 | tryptamine to tryptophol |
| 2J2 | arachidonic acid epoxidation |
| 4B1 | fatty acid ω-hydroxylation |
| 4A10* | lipid peroxidation |
| 2E1* | arachidonic acid ω-hydroxylation, lipid peroxidation |

TABLE 1-continued

CYP isozymes in human heart.

| | Physiologic Activity |
|---|---|
| 1B1* | 17-beta estradiol hydroxylation |
| 2F2* | natural substrate unknown |

If cardioprotection correlates more closely with protection for oxidative stress in isolated cardiomyocytes, then it is likely that the deleterious cytochrome P450 isozymes are present within the cardiomyocytes rather than endothelial cells. To measure superoxide production in frozen heart slices, unfixed human heart cryostat sections are stained with dihydroethidium to detect basal superoxide production. Parallel slices are treated with candidate cytochrome P450 inhibitors to assess their ability to suppress superoxide production. Cytochrome P450-dependent ROS production may be increased by first pretreating slides with hydrogen peroxide.

The cytochrome P450 isozyme(s) responsible for reperfusion injury in the rat heart is highly conserved across species, such as CYP 1B1, and that isozyme is present in human heart tissue, it is likely that the corresponding isozyme in humans is sensitive to the candidate inhibitors. Candidate cytochrome P450 isozymes in rat heart that are inhibited by chloramphenicol and sulfaphenazole can be detected using AMMC (a Gentest product) as a substrate. AMMC demethylase activity is inhibited by chloramphenicol and sulfaphenazole in concentration ranges that correspond closely to those needed for protection in the perfused heart model. While CYP2D2 and 2D6 are the most common enzymes that demethylate AMMC, they were not inhibited by sulfaphenazole in a recombinant system.

3. Vascular Tone in Coronary Artery Rings

During reperfusion, vasodilation is important to allow adequate re-oxygenation, while vasoconstriction perpetuates ischemia in distal tissues. The results described herein, demonstrating enhanced coronary flow during reperfusion, suggest that vasodilation is a feature of at least some cytochrome P450 inhibitors. To identify agents that confer protection in the heart, coronary artery ring segments from explanted vessels, e.g., human vessels (such as those obtained at the time of coronary artery bypass graft), can be employed as they contract in response to superoxide and relax in response to nitric oxide. Vascular tone is therefore a reflection of the balance of superoxide and nitric oxide. Inhibition of superoxide production from cytochrome P450 enzymes results in vasorelaxation which can be measured with a tensiometer. If necessary, the ring segment can first be subjected to ischemia and reperfusion by modifying the organ bath perfusion buffer to exacerbate superoxide production. As a correlation has been established between vasorelaxation and reduction of infarct size, cytochrome P450 inhibitors that enhance vasorelaxation likely reduce infarct size.

4. Papillary Muscle Segments

Papillary muscle segments from human heart may be removed at time of surgery and subjected to ischemia/reperfusion in an organ bath. Agents useful in the invention limit superoxide production (detected by DHE conversion) and reduce apoptosis (detected in histologic sections by TUNEL assay, see Gottlieb, 1994).

5. White Blood Cells and Platelets

One aspect of reperfusion injury is mediated by inflammation, including activated T cells, monocytes, mast cells, and likely also B cells and neutrophils. T cells can be activated by free radicals and therefore are likely to become activated during reperfusion. Therefore, peripheral white blood cells may be used to screen for efficacy of cytochrome P450 inhibitors. Lymphocytes, neutrophils, and monocytes are obtained from whole blood using standard methods. Activation is assessed by flow cytometry after exposure to the appropriate stimulus, using activation-specific antibodies. Agents that suppress ROS production from activated white blood cells are likely to be beneficial in reperfusion injury of any organ.

Platelet aggregation is another aspect of ischemia/reperfusion injury. It has been suggested that platelet activation may be triggered by ROS and arachidonic acid metabolites that may be generated by cytochrome P450 enzymes. Therefore, inhibition of cytochrome P450 enzymes in platelets may suppress aggregation, an effect which can be tested using platelet aggregometry and purified platelets from human blood, which are incubated in the presence or absence of various cytochrome P450 inhibitors.

D. Exemplary Agents

A number of agents may find use in the methods of the invention including, but not limited to, agents such as $H_2$-receptor antagonists, e.g., cimetidine, ranitidine, and ebrotidine; $H^+/K^+$ ATPase inhibitors, e.g., omeprazole; antimicrobials and antifungals, e.g., chloramphenicol, econazole, ketoconazole, sulfaphenazole, trimethoprim, sulfamethoxazole, clotrimazole, and miconazole; CNS-active agents including tricyclic antidepressants such as clomipramine, amitriptyline, and desipramine, serotonin reuptake inhibitor antidepressants such as fluoxetine, sertraline, and paroxetine, phenothiazine antipsychotics, e.g., chlorpromazine, and benzodiazepines anxiolytics, for instance, flurazepam and medazapam; NSAIDs, e.g., diclofenac, flufenamine, fenoprofen, flurbiprofen, and ketoprofen; metyrapone; 7-ethoxyresorufin; HMG-CoA synthase inhibitors, e.g., statins; sartans, and calcium channel blockers, e.g., diltiazem, verapamil, lercanidipine, nifedipine, nisoldipine, nicardipine, isradipine, nitrendipine, felodipine, and amlodipine, as well as agents that inhibit mitochondrial superoxide production, e.g., complex I inhibitors such as idebenone, rotenone, p-hydroxy-mercuribenzoat, rolliniastatin-2, capsaicin and amytal; complex III inhibitors, e.g., myxothiazol, antimycin A and mucidin (strobilurin A); and agents that inhibit superoxide production at other sites, for instance, xanthine oxidase inhibitors (e.g., allopurinol), and NAD(P)H oxidase inhibitors (e.g., apocynin and diphenyleneiodonium).

In particular, agents useful in the practice of the invention include, but are not limited to, agents that inhibit the amount (level) or activity of one or more cytochrome P450 enzymes. Exemplary inhibitors of cytochrome P540 enzymes may include H2-receptor antagonists, e.g., cimetidine, ranifidine, and ebrotidine; $H^+/K^+$ ATPase inhibitors, e.g., omeprazole; antimicrobials and antifungals, e.g., chloramphenicol, econazole, ketoconazole, sulfaphenazole, clotrimazole, and miconazole; CNS-active agents including tricyclic antidepressants such as clomipramine, amitriptyline, and desipramine; serotonin reuptake inhibitor antidepressants such as fluoxetine, sertraline, and paroxetine; phenothiazine antipsychotics, e.g., chlorpromazine; benzodiazepines anxiolytics, for instance, flurazepam and medazapam; NSAIDs, e.g., diclofenac, flufenamine, fenoprofen, flurbiprofen, and ketoprofen, metyrapone, 7-ethoxyresorufin: HMG-CoA synthase inhibitors, e.g., statins; sartans, and calcium channel blockers, e.g., diltiazem, verapamil, lercanidipine, nifedipine, nisoldipine, nicardipine, isradipine, nitrendipine, felodipine, and amlodipine.

Further, agents that can act as substrates or inhibitors of one or a subset of cytochrome P450 enzymes including, but not limited to, the cytochrome 450 1A family, e.g., 1A1 or 1A2, the cytochrome P450 2B family, e.g., 2B6 and 2B7, the cytochrome P450 2C family, e.g., 2C8-19 such as 2C9 or 2C19, the cytochrome P450 2D family, e.g., 2D6, the cytochrome P450 2E family, e.g., 2E1, the cytochrome P450 3A family, e.g., 3A4, 3A5 and 3A7, and the cytochrome P450 4B family, e.g., 4B1, may find use in the methods of the invention. For instance, resveratrol is an inhibitor of 1A1. For example, substrates of 1A2 include, but are not limited to, amitriptyline, caffeine, clomipramine, clozapine, cyclobenzaprine (Flexeril®), estradiol, fluvoxamine, haloperidol, imipramine N-DeMe, mexiletine, naproxen, ondansetron, phenacetin, acetaminophen, propranolol, riluzole, ropivacaine, tacrine, theophylline, veraprimil, warfarin, zileuton, and zolmitriptan. Inhibitors of 1A2 include, but are not limited to, amiodarone, cimetidine, fluoroquinolones, fluvoxamine, furafylline, methoxsalen, mibefradil and ticlopidine.

Substrates of 2B6 include bupropion, cyclophosphamide, ifosfamide and an inhibitor of 2B6 includes thiotepa. Substrates of 2C8 include TCA, diazepam and verapamil and cimetidine is an inhibitor of 2C8.

Substrates of 2C9 include NSAIDs such as diclofenac, ibuprofen, suprofen, meloxicam and S-naproxen, oral hypoglycemic agents such as tolbutamide and glipizide, angiotensin II blockers such as losartan (activated) and irebesartan; amitriptyline, celecoxib, fluoxetine, fluvastatin, glyberide, phenytoin, rosiglitazone, tamoxifen, torsemide, tolbutamide, piroxican, irbesartan, verapamil, dextromethorphan, and S-warfarin. Inhibitors of 2C9 include, but are not limited to, amiodarone, cimetidine, chloramphenicol, fluconazole, fluvastatin, fluvoxamine, isoniazid, ketoconazole, metronidazole, ritonavir, lovastatin, paroxetine, phenylbutazone, probenicid, sertraline, sulfamethoxazole, sulfaphenazole, teniposide, ticlopidine, trimethoprim, and zafirlukast.

Substrates of 2C19 include proton pump inhibitors such as lansoprazole, omeprazole, pantoprazole, and E-3810; anti-epileptics such as diazepam, nophenytoin(O), S-mephenytoin, and phenobarbitone, amitriptyline, citalopram, clomipramine, cyclophosphamide, hexobarbital, imipramine N-DeME, indomethacin, R-mephobarbital, mocolobemide, nelfinavir, nilutamide, primidone, progesterone, proguanil, propranolol, teniposide and R-warfarin. Inhibitors of 2C19 include cimetidine, felbamate, fluoxetine, fluvoxamine, indomethacin, ketoconazole, lansoprazole, modafinil, omeprazole, paroxetine, probenicid, ticlopidine, and topiramate.

Substrates of 2D6 include, but are not limited to, beta blockers such as caredilol, S-metoprolol, propafemone, timolol; antidepressants such as amitriptyline, clomipramine, desipramine, imipramine, paroxetine; antipsychotics such as haloperidol, perphenazine, risperidone, thioridazine, alprenolol, amphetamine, bufuraolol, chlorpheniramine, chlorpromazine, codeine, debrisoquine, dexfenfluramine, dextromethorphan, encainide, flecainide, fluoxetine, fluvoxamine, lidocaine, metoclopramide, methoxyamphteamine, mexiletine, notriptyline, minaprine, ondansetron, perhexiline, phenacetin, phenformin, propranolol, quanoxan, sparteine, tamoxifen, tramadol, and venlafaxine. Inhibitors of 2D6 include, but are not limited to, amiodarone, celcoxib, chlorpromazine, chlorpheniramine, cimetidine, clomipramine, cocaine, doxorubicin, fluxetine, halofantrine, red-haloperidol, levomepromazine, metoclopramide, methadone, mibefradil, moclobemide, paroxetine, quinidine, ranitidine, tironavir, sertraline and terbinafine.

Substrates of 2E1 include, but are not limited to, anesthetics such as enflurane, halothane, isoflurane, methoxyflurane, sevoflurane, and acetaminophen, aniline, benzene, chlorzoxazone, ethanol, N,N-dimethyl formamide, and theophylline. Inhibitors of 2E1 include, but are not limited to, diethyldithiocarbamate and disulfan.

Substrates of 3A 4, 5 and 7 include, but are not limited to, macrolide antibiotics such as clarithromycin, erythromycin, anti-arrhythmics such as quinidine, benzodiazepines such as alprazolam, diazepam, midazolam, and triazolam, immune modulators such as cyclosporine, tarolimus and FK506, antivirals such as indinavir, nelfinavir, ritonavir, and saquinavir, prokinetic cisaprine, antihistamines such as astemizole, chlorpheniramine, and terfenidine, calcium channel blockers such as amlodipine, diltiazem, felodipine, lercanidipine, nifedipine, nisoldipine, nitrendipine and verapamil, HMG CoA reductase inhibitors such as atorvastatin, cerivastatin, and lovastatin, estradiol, hydrocortisone, progesterone, testosterone, alfentanyl, buspirone, caffeine, cocaine, dapsone, codeine, N-demethylation, dextromethorphan, fentanyl finasteride, haloperidol, lidocaine, methadone, odanstron, pimozide, propranolol, quinine, salmeterol, sildenafil, tamoxifen, taxol, terfenadine, trazodone, vincristine, zaleplon, and zolpidem. Inhibitors of 3A 4, 5 and 7 include but are not limited to delaviridine, indinavir, nelfmavir, ritonavir, saquinavir, amiodarone, cimetidine, ciprofloxacin, clarithromycin, diethyl-dithiocarbamate, diltiazem, erythromycin, fluconazole, fluvoxamine, gestodene, itaconazole, ketoconazole, mifepristone, nefazodone, norfloxacin, norfluoxetine, mibefradil, and troleandomycin.

In one embodiment, the agent is selected from the group consisting of cimetidine, chloramphenicol, econazole, ketoconazole, sulfaphenazole, clotrimazole, miconazole, trimethoprim, sulfamethoxazole or trimethoprim/sulfamethoxazole.

In one embodiment, preferred agents do not substantially inhibit protein synthesis, e.g., in mitochondria. In one embodiment, the agent to be employed in the methods of the invention is not chloramphenicol (see He et al., 2001).

III. Exemplary Indications or Conditions to be Treated with the Therapeutic Agents To treat or inhibit reperfusion injury in a mammal, one or more agents of the invention may be administered after the onset of ischemia associated with any condition, such as those associated with production of ROS. The one or more agents may also be administered to a mammal at risk of having ischemia and reperfusion injury. For instance, the ischemia or condition can be associated with or caused by acute myocardial infarction, elective angioplasty, coronary artery bypass graft, surgery involving cardiac bypass or organ or tissue transplantation, e.g., cardiac transplantation, stroke, head trauma, drowning, sepsis, cardiac arrest, drowning or shock, atherosclerosis, hypertension, cocaine-induced heart disease, smoking-induced heart disease, heart failure, pulmonary hypertension, hemorrhage, capillary leak syndrome (such as child and adult respiratory distress syndrome), multi-organ system failure, a state of low colloid oncotic pressure (such as starvation, anorexia nervosa, or hepatic failure with decreased production of serum proteins), anaphylaxis, hypothermia, cold injury, e.g., due to hypothermic perfusion, frostbite, hepatorenal syndrome, delirium tremens, a crush injury, mesenteric insufficiency, peripheral vascular disease, claudication, burn, electrocution, excessive drug-induced vasodilation, excessive drug-induced vasoconstriction, tissue rejection after transplantation, graft versus host disease, radiation exposure, e.g., during fluoroscopy or radiographic imaging, or exposure to high energy, e.g., exposure to laser light. Excessive drug-induced vasodilation can be caused by, for instance, nitroprusside, hydralazone, dyazoxide, a calcium channel blocker, or a general anesthetic. Excessive drug-induced vasoconstriction can be caused by, for instance, neosynephrine, isoproterenol, dopamine, dobutamine, or cocaine.

In one embodiment, one or more agents of the invention are employed to treat or inhibit reperfusion injury associated with a vascular interventional procedure. Vascular interventional procedures include, but are not limited to, those which employ a stent, e.g., a coated stent, angioplasty catheter (percutaneous transluminal angioplasty), laser catheter, atherectomy catheter, e.g., TEC and DVI, angioscopy device, beta or gamma radiation catheter, intravascular ultrasound device, rotational atherectomy device, radioactive balloon, heatable wire, heatable balloon, biodegradable stent strut, or biodegradable sleeve.

For instance, the agents of the invention are useful to inhibit or treat indications associated with upregulation of cytochrome P450 enzymes including but not limited to hypertension, obesity, drug, e.g., cocaine, use, heart failure, and in tobacco smokers and diabetics, as smokers and diabetics are prone to more severe coronary artery disease and stroke. In one embodiment of the invention, patients with these indications are chronically treated with one or more agents of the invention to decrease their risk of an adverse cardiovascular event. In another embodiment, one or more agents of the invention are administered chronically to slow down the progression of heart failure. For example, cardiac conditions may be inhibited or treated with inhibitors of cytochrome P450 enzymes expressed in the heart, e.g., CYP 1A1, 2B6/7, 2C8-19, e.g., 2C9, 2D6, 2E1, and 4B1. For instance, as heart failure is associated with upregulation of CYP2J2, CYP1B1, CYP2E1, CYP4A10, and CYP2F2, heart failure patients may be treated with one or more inhibitors of one or more of those enzymes. As drug use induces CYP 1A1 and 2J2 in cardiac tissues, one or more inhibitors of those enzymes may be cardioprotective in drug users. Also, as CYP4A10 and CYP2E1 are upregulated in obese patients, inhibitors of those enzymes may likewise be efficacious.

Moreover, patients who experience one myocardial infarction have a high probability of having subsequent myocardial infarctions. Therefore, in one embodiment, patients who survive a myocardial infarction are chronically treated with one or more agents of the invention to decrease their risk of recurrence. Similarly, one or more agents of the invention may be administered chronically to patient with stroke or peripheral vascular disease. Further, as cytochrome P450 enzyme expression is sexually dimorphic and men are at increased risk of cardiovascular disease, selective inhibition of male-specific cytochrome P450 isozymes may be useful to decrease cardiac risk.

In addition, since cytochrome P450 enzymes can be triggered to generate excessive reactive oxygen species (ROS) in response to hypoxia or oxidative stress, one or more agents of the invention may be administered to a mammal before, during, or after chemotherapy, radiation therapy, or laser treatments, or to a mammal diagnosed with alcohol intoxication, burn injuries, sepsis, retinopathy of the premature, hyperoxia, infantile respiratory distress syndrome, necrotizing enterocolitis, intravascular hemolysis, acute respiratory distress syndrome, Alzheimers disease, Parkinson's disease, and related neurodegenerative diseases, autoimmune diseases such as lupus and rheumatoid arthritis, and chronic inflammatory processes such as atherosclerosis. Inhibition of specific cytochrome P450 isozymes in these conditions decreases ROS production and attenuates tissue damage that contributes to pathogenesis.

Thus, in one embodiment, the therapeutic agents can be used prophylactically in a mammal after a cardiovascular event, or in a mammal at risk of an ischemic event including but not limited to a smoker, diabetic, a mammal with hypertension, dyslipidemia, or a family history of vascular events, as well as in a mammal with documented coronary disease, peripheral vascular disease, or cerebrovascular disease, or in a mammal prior to diagnostic or therapeutic radiology, or prior to laser therapy, for instance, cutaneous or retinal laser therapy.

IV. Dosages, Formulations and Routes of Administration of Therapeutic Agents

The therapeutic agents of the invention, including their pharmaceutically acceptable salts, are administered so as to achieve a desired effect, e.g., inhibit or reduce ischemia and/or reperfusion injury, increase cardiac contractility, increase coronary blood flow, reduce superoxide production, or reactive oxygen specie production including lipid peroxidation, reduce CK release, inhibit or reduce infarct size, and/or inhibit or decrease the level or activity of one or more cytochrome P450 isozymes. To achieve the desired effect(s), the agent, or a combination thereof, may be administered as single or divided dosages. The amount administered will vary depending on various factors including, but not limited to, the agent chosen, the indication or condition to be prevented or treated, the weight, physical condition, health, and age of the mammal, and whether prevention or treatment is to be achieved. Such factors can be readily determined by the clinician employing animal models or other test systems that are available in the art. For agents which inhibit cytochrome P450 enzymes, a preferred amount is one which is chosen to selectively inhibit one or more cytochrome P450 enzymes. For example, the amount of clotrimazole or proadifen employed in the methods of the invention does not include the high doses described in Zhang et al. (1999).

Thus, the administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration may be prophylactic in a patient at risk of ischemic and/or reperfusion injury, e.g., a patient at risk of myocardial infarction may self-administer an agent of the invention, or in response to certain symptoms associated with ischemic and/or reperfusion injury in an ambulance or emergency room prior to clinical confirmation of the injury. Other conditions for which prophylactic administration of the therapeutic agents may be indicated include but are not limited to smokers, diabetics, a mammal with hypertension, dyslipidemia, or a family history of vascular events, as well as in mammals with documented coronary disease, peripheral vascular disease, or cerebrovascular disease, and/or in a mammal after a cardiovascular event, prior to diagnostic or therapeutic radiology, or prior to laser therapy, for instance, cutaneous or retinal laser therapy. The administration of the agents of the invention may be essentially continuous over a preselected period of time or may be in a series of spaced doses. Both local and systemic administration is contemplated.

To prepare the composition, agents are synthesized or otherwise obtained, purified as necessary or desired and then optionally lyophilized and stabilized. The agent can then be adjusted to the appropriate concentration, and optionally combined with other agents.

Thus, one or more suitable unit dosage forms comprising the therapeutic agents of the invention can be administered by a variety of routes including oral, parenteral (including subcutaneous, intravenous, intramuscular and intraperitoneal), rectal, dermal, buccal, mucosal, transdermal, intrathoracic, intrapulmonary and intranasal (respiratory) routes. The therapeutic agents may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system. In general, such doses and dosage forms comprise an amount of at least one of the agents of the invention effective to treat or prevent the clinical symptoms of a specific indication or condition. Any statistically significant attenuation of one or more symptoms of an indication or condition that has been treated pursuant to the method of the present invention is considered to be a treatment of such indication or condition within the scope of the invention.

When the therapeutic agents of the invention are prepared for oral administration, they are generally combined with a pharmaceutically acceptable carrier, diluent or excipient to form a pharmaceutical formulation, or unit dosage form. For oral administration, the agents may be present as a powder, a granular formulation, a solution, a suspension, an emulsion or in a natural or synthetic polymer or resin for ingestion of the active ingredients from a chewing gum. The active agents may also be presented as a bolus, electuary or paste. Orally administered therapeutic agents of the invention can also be formulated for sustained release, e.g., the agents can be coated, micro-encapsulated, or otherwise placed within a sustained delivery device. The total active ingredients in such formulations comprise from 0.1 to 99.9% by weight of the formulation.

Pharmaceutical formulations containing the therapeutic agents of the invention can be prepared by procedures known in the art using well-known and readily available ingredients. For example, the agent can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montinorillonites, and the like.

For example, tablets or caplets containing the agents of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing at least one agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more agents of the invention are designed to resist disintegration in the stomach and dissolve in the more neutral to alkaline environment of the duodenum.

The therapeutic agents of the invention can also be formulated as elixirs or solutions for convenient oral administration or as solutions appropriate for parenteral administration, for instance by intramuscular, subcutaneous, intraperitoneal or intravenous routes. The administration may be accomplished via a needle, a catheter, e.g., a balloon catheter, which is distal to the region to be treated, for instance, a coronary artery, a stent or a stent coated with the agent, such as an intracoronary stent, which may be useful for sustained release of the agent. The pharmaceutical formulations of the therapeutic agents of the invention can also take the form of an aqueous or anhydrous solution or dispersion, or alternatively the form of an emulsion or suspension or salve.

Thus, the therapeutic agents may be formulated for parenteral administration (e.g., by injection, for example, bolus injection or continuous infusion) and may be presented in unit dose form in ampules, pre-filled syringes, small volume infusion containers or in multi-dose containers. As noted above, preservatives can be added to help maintain the shelve life of the dosage form. The active agents and other ingredients may form suspensions, solutions, or emulsions in oily or aqueous vehicles, and may contain formulatory agents such as suspending, stabilizing and/or dispersing agents. Alternatively, the active agents and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers, vehicles and adjuvants that are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$-$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

It is possible to add, if necessary, an adjuvant chosen from antioxidants, surfactants, other preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added.

Also contemplated are combination products that include one or more agents of the present invention and one or more other therapeutic agents.

Additionally, the agents are well suited to formulation as sustained release dosage forms and the like. The formulations can be so constituted that they release the active agent, possibly over a period of time. Coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, draining devices and the like.

For topical administration, the therapeutic agents may be formulated as is known in the art for direct application to a target area, e.g., chest. Forms chiefly conditioned for topical application take the form, for example, of creams, milks, gels, dispersion or microemulsions, lotions thickened to a greater or lesser extent, impregnated pads, ointments or sticks, aerosol formulations (e.g., sprays or foams), soaps, detergents, lotions or cakes of soap. Other conventional forms for this purpose include wound dressings, coated bandages or other polymer coverings, ointments, creams, lotions, pastes, jellies, sprays, and aerosols. Thus, the therapeutic agents of the invention can be delivered via patches or bandages for dermal administration. Alternatively, the agent can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

As described above, the therapeutic agents of the invention can be delivered via patches for transdermal administration. See U.S. Pat. No. 5,560,922 for examples of patches suitable for transdermal delivery of a therapeutic agent. Patches for transdermal delivery can comprise a backing layer and a polymer matrix which has dispersed or dissolved therein a therapeutic agent, along with one or more skin permeation enhancers. The backing layer can be made of any suitable material which is impermeable to the therapeutic agent. The backing layer serves as a protective cover for the matrix layer and provides also a support function. The backing can be formed so that it is essentially the same size layer as the polymer matrix or it can be of larger dimension so that it can extend beyond the side of the polymer matrix or overlay the side or sides of the polymer matrix and then can extend outwardly in a manner that the surface of the extension of the backing layer can be the base for an adhesive means. Alternatively, the polymer matrix can contain, or be formulated of, an adhesive polymer, such as polyacrylate or acrylate/vinyl acetate copolymer. For long-term applications it might be desirable to use microporous and/or breathable backing laminates, so hydration or maceration of the skin can be minimized.

Examples of materials suitable for making the backing layer are films of high and low density polyethylene, polypropylene, polyurethane, polyvinylchloride, polyesters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the adhesive polymer matrix.

The backing layer can be any appropriate thickness which will provide the desired protective and support functions. A suitable thickness will be from about 10 to about 200 microns.

Generally, those polymers used to form the biologically acceptable adhesive polymer layer are those capable of forming shaped bodies, thin walls or coatings through which therapeutic agents can pass at a controlled rate. Suitable polymers are biologically and pharmaceutically compatible, nonallergenic and insoluble in and compatible with body fluids or tissues with which the device is contacted. The use of soluble polymers is to be avoided since dissolution or erosion of the matrix by skin moisture would affect the release rate of the therapeutic agents as well as the capability of the dosage unit to remain in place for convenience of removal.

Exemplary materials for fabricating the adhesive polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, crosslinked polymethacrylate polymers (hydrogel), polyvinylidene chloride, poly(ethylene terephthalate), butyl rubber, epichlorohydrin rubbers, ethylenvinyl alcohol copolymers, ethylene-vinyloxyethanol copolymers; silicone copolymers, for example, polysiloxane-polycarbonate copolymers, polysiloxane-polyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxy propyl methyl cellulose, and cellulose esters; polycarbonates; polytetrafluoroethylene; and the like.

Preferably, a biologically acceptable adhesive polymer matrix should be selected from polymers with glass transition temperatures below room temperature. The polymer may, but need not necessarily, have a degree of crystallinity at room temperature. Cross-linking monomeric units or sites can be incorporated into such polymers. For example, cross-linking monomers can be incorporated into polyacrylate polymers, which provide sites for cross-linking the matrix after dispersing the therapeutic agent into the polymer. Known cross-linking monomers for polyacrylate polymers include polymethacrylic esters of polyols such as butylene diacrylate and dimethacrylate, trimethylol propane trimethacrylate and the like. Other monomers which provide such sites include allyl acrylate, allyl methacrylate, diallyl maleate and the like.

Preferably, a plasticizer and/or humectant is dispersed within the adhesive polymer matrix. Water-soluble polyols are generally suitable for this purpose. Incorporation of a humectant in the formulation allows the dosage unit to absorb moisture on the surface of skin which in turn helps to reduce skin irritation and to prevent the adhesive polymer layer of the delivery system from failing.

Therapeutic agents released from a transdermal delivery system must be capable of penetrating each layer of skin. In order to increase the rate of permeation of a therapeutic agent, a transdermal drug delivery system must be able in particular to increase the permeability of the outermost layer of skin, the stratum corneum, which provides the most resistance to the penetration of molecules. The fabrication of patches for transdermal delivery of therapeutic agents is well known to the art.

The therapeutic agent may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active agents can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-85% by weight.

Drops, such as eye drops or nose drops, may be formulated with one or more of the therapeutic agents in an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0-8.0.

The agents of the invention can also be administered to the respiratory tract. Thus, the present invention also provides aerosol pharmaceutical formulations and dosage forms for use in the methods of the invention. Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatine or blister packs from which the powder may be administered with the aid of an inhalator, insufflator, or a metered-dose inhaler (see, for example, the pressurized metered dose inhaler (MDI) and the dry powder inhaler disclosed in Newinan (1984). Aromatic oils may also be administered.

Therapeutic agents of the present invention can also be administered in an aqueous solution when administered in an aerosol or inhaled form. Thus, other aerosol pharmaceutical formulations may comprise, for example, a physiologically acceptable buffered saline solution containing between about 0.1 mg/ml and about 100 mg/ml of one or more of the agents of the present invention specific for the indication or condition to be treated. Dry aerosol in the form of finely divided solid particles that are not dissolved or suspended in a liquid are also useful in the practice of the present invention. Agents of the present invention may be formulated as dusting powders and comprise finely divided particles having an average particle size of between about 1 and 5 µm, alternatively between 2 and 3 µm. Finely divided particles may be prepared by pulverization and screen filtration using techniques well known in the art. The particles may be administered by inhaling a predetermined quantity of the finely divided material, which can be in the form of a powder. It will be appreciated that the unit content of active ingredient or ingredients contained in an individual aerosol dose of each dosage form need not in itself constitute an effective amount for treating the particular indication or condition since the necessary effective amount can be reached by administration of a plurality of dosage units. Moreover, the effective amount may be achieved using less than the dose in the dosage form, either individually, or in a series of administrations.

For administration to the upper (nasal) or lower respiratory tract by inhalation, the therapeutic agents of the invention are conveniently delivered from a nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627. Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.). For intra-nasal administration, the therapeutic agent may also be administered via nose drops, a liquid spray, such as via a plastic bottle atomizer or metered-dose inhaler. Typical of atomizers are the Mistometer (Wintrop) and the Medihaler (Riker).

Furthermore, the active ingredients may also be used in combination with other therapeutic agents, for example, pain relievers, anti-inflammatory agents, agents that inhibit protein synthesis, e.g., antimicrobials such as erythromycin and its derivatives, tetracycline and its derivatives, puromycin and its derivatives, lincomycin and its derivatives, and streptomycin; complex I inhibitors such as idebenone, rotenone, p-hydroxy-mercuribenzoat, roliniastatin-2, capsaicin and amytal, complex III inhibitors, e.g., myxothiazol, antimycin A and mucidin (strobilurin A); and agents that inhibit superoxide production, for instance, xanthine oxidase inhibitors (e.g., allopurinol), and NAD(P)H oxidase inhibitors (e.g., apocynin and diphenyleneiodonium, antihistamines, bronchodilators and the like, whether for the conditions described or some other condition.

The present invention further pertains to a packaged pharmaceutical composition such as a kit or other container. The kit or container holds a therapeutically effective amount of an agent of the invention and instructions for using the pharmaceutical composition for a particular indication or condition. The pharmaceutical composition includes at least one agent of the present invention, in an effective amount.

The invention will be further described by the following non-limiting examples.

EXAMPLE I

Materials and Methods

Langendorff Perfusion and Global Ischemia/Reperfusion.

The global ischemia protocol was adapted from that of Tsuchida et al. (1994). All procedures were approved by the Animal Care and Use Committee at The Scripps Research Institute (TSRI). To obtain isolated hearts, hearts were excised from an anesthetized mammal such as a rabbit and quickly cannulated onto the Langendorff perfusion apparatus. The heart is perfused with Krebs-Ringer buffer for 15 minutes before ischemia/reperfusion episodes. No-flow ischemia is maintained for 30 minutes and reperfusion is accomplished by restoring flow for 15 minutes (unless otherwise indicated). Ischemic preconditioning can be induced by three 5 minute cycles of no-flow ischemia and reperfusion immediately preceding the regular ischemia and reperfusion.

In brief, the heart was excised from the anesthetized rabbit and quickly cannulated onto the Langendorff perfusion apparatus. The heart was perfused with Krebs-Ringer buffer for 15 minutes before ischemia/reperfusion episodes. No-flow ischemia was maintained for 30 minutes and reperfusion was accomplished by restoring flow for 15 minutes (unless otherwise indicated). Ischemic preconditioning was induced by three 5 minute cycles of no-flow ischemia and reperfusion immediately preceding the regular ischemia and reperfusion. The efficacy of these interventions was verified by measurement of creatine kinase (CK) release and infarct size measurement using triphenyl tetrazolium chloride (TTC) staining (Pain et al., 2000; Downey, 2001).

Isolation of Mitochondria and Cytosol.

Upon completion of global ischemia, the heart was removed from the cannula and the ventricles were minced in 20 mL per heart of ice-cold MSE buffer (225 mmol/L, mannitol, 75 mmol/L sucrose, 1 mmol/L EGTA, 1 mmol/L $Na_3VO_4$, and 20 mmol/L HEPES-KOH [pH 7.4]). The heart was further polytron-homogenized for 5 seconds at maximal power output by a PowerGen 125 (Fisher Scientific) equipped with a 10 mm diameter rotor knife. The homogenate was centrifuged for 10 minutes at 600 g, 4° C. The pellet was discarded and the supernatant was centrifuged for 10 minutes at 10,000 g to pellet mitochondria and lysosomes. The supernatant (crude cytosol) was further centrifuged for 30 minutes at 100,000 g to obtain particulate-free cytosol (S100). The 10,000 g pellet from the previous centrifugation was resuspended in 10 mL of MSE buffer and centrifuged for 10 minutes at 8000 g. This wash step was repeated once. The final pellet was resuspended in 3 mL of MSE buffer and was further purified by hybrid Percoll/metrizamide discontinuous gradient purification consisting of 5 mL of 6% Percoll, 2 mL of 17% metrizamide, and 2 mL of 35% metrizamide, all prepared in 0.25 mol/L sucrose and set up in 13 mL tubes (Storrie et al., 1996).

Three milliliters of the sample was overlaid on top of the gradient and centrifuged for 20 minutes at 50,000 g, 4° C., using a Beckman SW41 rotor. The mitochondrial fraction at the interface between 17% and 35% metrizamide was collected and diluted at least 10-fold with MSE buffer, followed by centrifugation for 10 minutes at 10,000 g to remove metrizamide. The pellet was resuspended in 20 mL of MSE buffer and centrifuged again. The final pellet was resuspended in 3 mL of MSE buffer and aliquots were stored at −80° C. Protein concentration was determined using the Bradford assay, and for all experiments, equal amounts of mitochondrial protein were loaded on the gels. Cytosol concentrations were adjusted to be equal in all conditions before incubating with mitochondria.

Suborganellar Fractionization of Mitochondria.

A modification of the method of Comte and Gautheron (1979) was used to fractionate mitochondria. Freshly isolated purified mitochondria were pelleted by centrifugation for 5 minutes at 10,000 g. The mitochondrial pellet was resuspended in 10 mM $KH_2PO_4$, pH 7.4, and incubated on ice for 20 minutes for hypotonic swelling. The mitochondria were centrifuged for 15 minutes at 10,000 g, 4° C. to pellet mitoplasts (inner membrane and matrix). The supernatant, containing outer membrane (OM) and intermembrane space (IMS), was centrifuged for 30 minutes at 100,000 g to separate OM (pellet) and IMS (supernatant). The mitoplast pellet was resuspended in 500 µl of MC buffer (300 mM sucrose, 1 mM EGTA, 1 mM $Na_3VO_4$, 20 mM MOPS, pH 7.4) and sonicated on ice in 5 cycles of 20 second bursts and 40 second rest intervals with output setting at 8-10 Watts. The sonicated mitoplast preparation was centrifuged for 10 minutes at 10,000 g to remove any remaining intact mitoplasts or mitochondria, followed by centrifugation at 100,000 g for 30 minutes to separate inner membrane (IM) and matrix (MTX).

Metabolic Inhibition of Adult Cardiomyocytes.

The isolation of adult rabbit cardiomyocytes and metabolic inhibition were conducted as described by Gottlieb et al. (1996). Cardiomyocytes were disrupted by nitrogen cavitation (Gottlieb et al., 2000). The mitochondria and cytosol were isolated as above except that no gradient purification was used (He et al., 1999).

Labeling, Purification, and Identification of Mitochondrial Phosphoprotein.

For phosphorylation reactions, 100 µg of purified mitochondria was incubated in MSE buffer supplemented with 25 mmol/L HEPES-KOH [pH 7.5], 10 mmol/L magnesium acetate, 10 µmol/L ATP (cold), and 10 µCi [γ-$^{32}$P]ATP for 30 minutes at 30° C. with or without 250 µg of cytosol. The reaction mixture was subsequently centrifuged for 5 minutes at 10,000 g. The mitochondrial pellet was resuspended in 500 µL of MC buffer and washed twice. The mitochondrial proteins were resolved on a 12% polyacrylamide gel, transferred to nitrocellulose, and detected by autoradiography.

For protein kinase inhibition experiments, cytosols were incubated with the inhibitors at the indicated concentrations, then mitochondria were added and the reaction was initiated with the addition of ATP. Serine/threonine kinase inhibitors (Calbiochem, catalog No. 539572) included bisindolylmaleimide I, 10 nmol/L; H-89, 48 µmol/L; protein kinase G inhibitor, 86 µmol/L; ML-7, 0.3 µmol/L; KN-93, 0.37 µmol/L; and staurosporine, 10 nmol/L. Tyrosine kinase inhibitors (Calbiochem, catalogue No. 657021) included genistein, 25 µmol/L; PP2, 5 nmol/L; AG490, 15 µmol/L; AG1296, 1 µmol/L; and AG1478, 3 nmol/L.

2D Gel Electrophoresis, Mass Spectrometry, and Phosphoamino Acid Analysis.

Determination of Phosphoamino Acids.

To determine the phosphorylated amino acid(s) of EF-$Tu_{mt}$, the radiolabeled protein was excised from a PVDF membrane and subjected to acid hydrolysis. The hydrolyzed mixture was subjected to 1-D electrophoresis on a thin-layer cellulose plate (Murry et al., 1986).

To prepare p46 for identification by mass spectrometry, 14 mg of metrizamide-purified mitochondria were obtained from two untreated hearts. Two aliquots of mitochondria (7 mg each) were subjected to phosphorylation as above, except one of the aliquots was phosphorylated with non-radioactive ('cold') ATP. Following the reaction, the mitochondria of both reactions were subjected to suborganellar fractionation as described above to obtain the IM. IM was chosen as the source for identification of p46 because of its small volume for subsequent 2D gel analysis and the reasonable abundance of p46. Hot and 'cold' IM were resuspended in buffer containing 8 M urea and 20 mM Tris-HCl (pH 7.4) and resolved by 2D gel electrophoresis under identical conditions using the Pharmacia IPGphor IEF system. Both gels were Coomassie-blue stained and dried. The gel containing the radiolabeled sample was exposed to X-ray film to localized p46. Using position markers, the autoradiogram was superimposed on the gel. Three closely spaced radioactive spots were found to precisely overlie three Coomassie blue-stained spots. These spots were located in a relatively "clean" portion of the gel with few other spots nearby, making their recognition straightforward. The same three spots on the non-radioactive gel were visually identified, confirmed by overlay of the autoradiograph, and excised for mass spectrometry analysis.

In-gel Digest of p46.

Tryptic in-gel digest of all three spots was performed as described in DiLisa et al. (1998). Unseparated tryptic peptide mixtures were diluted with 50% acetonitrile-5% trifluoroacetic acid to a final volume of 15 μl.

MALDI Analysis.

MALDI analysis was performed as described in DiLisa et al. (1998) using a Voyager DE-Str MALDI-TOF instrument (Applied Biosystems, Framingham, Mass.) equipped with a nitrogen laser (337 nm), operated in a delayed-extraction (Kay et al., 1997) and reflectron mode (Ferrain, 1996). Mass spectra were calibrated internally on the trypsin autolysis peptides.

Peptide Sequencing by MS/MS Analysis.

For MS/MS analysis, the crude peptide mixture obtained after in-gel digest was purified over a $C_{18}$ reversed-phase Zip-Tip® (Millipore; Bedford, Mass.). The purified sample was supplied into a nanospray needle (Protana, Odense; Denmark) and analyzed on a Q-Star quadrupole time-of-flight instrument (Sciex, Toronto; Canada) in nanospray mode. The ion spray voltage was set to 1100V. For MS/MS experiments the collision energy $Q_0$ was set to 50.

Column Chromatography Purification of EF-Tu and Detection of p46.

Mitochondria were labeled with [γ-$^{32}$P]ATP and fractionated as above to obtain the matrix fraction. The mitochondrial matrix components were resolved by anion exchange chromatography on a 1 mL DEAE-Sepharose Fast-Flow column (Pharmacia) and eluted with a stepwise salt gradient (40 to 500 mmol/L KCl, in steps of 10 mmol/L, in a buffer containing 20 mmol/L Tris HCl, pH 7.4). Fractions (0.5 mL) were collected, concentrated, and buffer-exchanged to 40 mmol/L KCl in 20 mmol/L Tris HCl [pH 7.4] by use of a centrifugal filter concentrator (Ultrafree-4, Millipore). Protein fractions were resolved by 12% SDS-PAGE. Immunoblot analysis for EF-Tu was performed as described in Woriax et al. (1997).

Infarct Size Measurement.

The measurement of infarct size was essentially identical to that detailed by Downey (2001) except for the method of quantitation. After the TTC reaction, the heart slices were scanned into TIFF files and analyzed with Adobe Photoshop 5.5. The images were digitally manipulated in an identical manner to ensure equivalent outcome. The brightness and contrast were adjusted so that in the histogram essentially only red and white colors remained on the spectrum, corresponding to noninfarcted and infarcted regions, respectively. The histogram counts of red and white were recorded. The percent infarction was calculated as white counts divided by the sum of red plus white counts. To examine the effect of chloramphenicol (CAP) on infarction, 100 μg/mL CAP was included in the buffer throughout the entire procedure: 15 minutes of stabilization, 30 minutes of global ischemia, and 2 hours of reperfusion (Downey, 2001). As a control for the possible interference of CAP with TTC staining, CAP was added to the last 15 minutes of the 2 hour reperfusion.

Sequencing of EF-Tu$_{mt}$ from Rabbit Heart cDNA.

Rabbit heart cDNA library (Stratagene, La Jolla, Calif.) was used as template to PCR amplify rabbit EF-Tu cDNA. The primers were based upon the bovine sequence, the sequence of the forward primer is: 5'-agcatgtggtggtgtatgtga-3' (SEQ ID NO: 1) and the reverse primer is: 5'-tgtggaacatct-caatgcctg-3' (SEQ ID NO:2). The PCR products thus obtained were then subcloned into PCR-2.1 vector (Q-biogene, Carlsbad, Calif.) for automated sequencing at The Scripps Research Institute Department of Molecular and Experimental Medicine DNA Core Lab.

TABLE 1

| | Phosphorylation of p46 | | |
|---|---|---|---|
| | Control | MI | PC |
| | 1 | 1.46 | 0.95 |
| | 1 | 1.18 | 0.62 |
| | 1 | 1.61 | 1.17 |
| | 1 | 1.69 | — |
| | 1 | 1.13 | 0.93 |
| Mean | 1 | 1.41 | 0.92 |
| SD | — | 0.25 | 0.23 |
| N | 5 | 5 | 4 |
| P(versus control) | — | <0.01 | NS |

Mitochondria from control, ischemic (MI), or preconditioned (PC) hearts were labeled with [γ-$^{32}$P]ATP, then washed and resolved by SDS-PAGE. Autoradiograms were scanned using a PhosphorImager and pixel density was compared across lanes. In each experiment, the control was normalized to a value of 1.
NS indicates not significant.

Results

The phosphorylation pattern of mitochondrial proteins was analyzed in hearts subjected to global ischemia for 30 minutes followed by the reperfusion for 15 minutes and compared with control perfused hearts and those subjected to preconditioning before ischemia and reperfusion. Because [γ-$^{32}$P] orthophosphate labeling of whole hearts was impractical, mitochondria were prepared from hearts and incubated with [γ-$^{32}$P]ATP. Phosphorylation of a number of mitochondrial proteins was observed, but mitochondria from ischemic hearts consistently demonstrated greater phosphorylation (1.4-fold, P<0.01) of a single protein of 46 kDa (see Table 1). The extent of phosphorylation of this protein (designated p46) from preconditioned hearts was not significantly different from control hearts. These results indicate that phosphorylation of p46 is inversely regulated by ischemia/reperfusion and preconditioning.

To determine if phosphorylation of p46 was regulated by cytosolic factors, cytosol was prepared from isolated control perfused hearts and from hearts subjected to global ischemia and reperfusion. These cytosols were then incubated with freshly isolated mitochondria from a normal rabbit heart, in the presence of [γ-$^{32}$P]ATP. Phosphorylation of p46 in the presence of control cytosol was quite low but increased when normal mitochondria were incubated in the presence of cytosol from ischemic hearts. Mitochondria incubated in the absence of any cytosol also demonstrated phosphorylation of p46, suggesting that a factor present in normal cytosol suppressed phosphorylation of p46 by an endogenous kinase.

To verify that this phosphorylation activity is associated with cardiomyocytes and not due to other cell types in the heart, cytosol was prepared from isolated adult rabbit cardiomyocytes incubated in the presence or absence of metabolic inhibitors (2-deoxyglucose and KCN) (He et al., 1999). Cytosol from the control cardiomyocytes again suppressed the phosphorylation of p46. However, cytosol from the metabolically inhibited cardiomyocytes, either during metabolic inhibition or 10 minutes after recovery, was unable to inhibit the phosphorylation of the 46-kDa mitochondrial protein.

Previously, it was shown that JNK immunoreactivity and kinase activity translocated to mitochondria after ischemia/reperfusion but not after ischemia alone (He et al., 1999). Although p46 phosphorylation could be detected in the absence of metabolic recovery, it was unknown whether JNK mediated phosphorylation of p46. To examine this possibility, cytosol was immunodepleted of JNK or p38 mitogen-activated protein kinase (MAPK). Mitochondria were then incubated with immunodepleted control or ischemic cytosol in the presence of [γ-$^{32}$P]ATP. Immunodepletion of JNK or p38 MAPK did not attenuate the increase in phosphorylation mediated by ischemic cytosols, indicating that neither of these protein kinases participates in the phosphorylation.

To gain additional information about the possible signal transduction pathway involved, the mitochondria were incubated with control or ischemic cytosols in the presence of a variety of kinase inhibitors and the effect on phosphorylation of p46 in the mitochondria assessed. A panel of serine/threonine kinase inhibitors was tested, which included the broad-spectrum inhibitor staurosporine, and inhibitors of protein kinase C (PKC), PKA, $Ca^{2+}$/calmodulin (CaM) kinase II, myosin light chain kinase, and PKG. Mitochondria are recognized to have an associated protein kinase A that is anchored to the membrane by an A-kinase anchoring protein (AKAP). However, H-89, a PKA inhibitor, did not affect phosphorylation of p46 (data not shown), suggesting that PKA was not involved. None of the inhibitors in the serine/threonine kinase panel suppressed phosphorylation of p46. Tyrosine kinase inhibitors were then tested, including genistein, a broad-range inhibitor effective against EGFR and src; PP2, an inhibitor of p56 (lck), p59 (fynI), and Hck; and AG490, an inhibitor of JAK2. The only inhibitor that reduced phosphorylation was genistein (n=3). To distinguish between a tyrosine kinase in cytosol and one endogenous to the mitochondria, we incubated mitochondria from an ischemic heart with genistein and found that again genistein was able to inhibit the phosphorylation of p46.

To identify p46, the inner-membrane proteins of control and ischemic cytosol-treated mitochondria were analyzed by 2D SDS-PAGE gels under identical conditions. The isoelectric point (pI) of p46 appeared to be about 6.5. In a preparative 2D gel for mass spectrometry analysis, three closely spaced Coomassie-stained spots on the 2D gel of inner-membrane proteins corresponding to radiolabeled p46 on the autoradiograph were selected for analysis by MALDI mass spectrometry.

The obtained MALDI spectra from the three spots of interest revealed that all three spots represented the same protein. A total of 12 mass fingerprints were obtained and were subjected to a database search, but no protein could be successfully matched. Therefore, the sample obtained from the middle gel spot was further analyzed by nanoelectrospray mass spectrometry (MS). All peptide mass fingerprints that were observed by MALDI analysis were also found in the nanoelectrospray MS spectrum. All peptides were observed as double-charged ions were analyzed in separate MS/MS experiments. Not all peptides fragmented in a way that a complete ion series could be obtained. Four of the analyzed peptides fragmented well enough to allow complete or partial sequencing. One peptide consisting of 12 amino acids was sequenced completely, yielding AEAGDNI(L)GAI(L)VR (SEQ ID NO:7) ("L" in parenthesis represents the possible alternative, because MS/MS is not able to distinguish residues I and L). The sequence I(L)I(L)DAVTYIPV (SEQ ID NO:8) was obtained from a second peptide of 13 amino acids, which was sequenced except for the last three residues. Two more peptides were partially sequenced yielding 6 and 4 amino acids, which are, respectively, EEI(L)DNA (SEQ ID NO:9) and YVSE (SEQ ID NO:10).

The two longer-sequenced peptides were subjected to a BLAST search and were fully matched (100%) with the human and the bovine mitochondrial precursor of the elongation factor Tu (SwissProt accession numbers P49411 and P49410, respectively). Although the rabbit sequence is not in the database, the EF-Tu sequence is highly conserved between human and bovine (>94% identity). A partial cDNA sequence for rabbit EF-Tu$_{mt}$ was obtained by PCR using primers corresponding to the bovine sequence for EF-Tumt were used for PCR synthesis using rabbit heart cDNA as template and a partial sequence was obtained (data not shown). For the partial sequence obtained, rabbit shares 92% homology with the human sequence and 95% homology with bovine at the amino acid level. One peptide sequence obtained by mass spectrometry fell within the partial cDNA sequence and matched exactly.

Figure 5A:
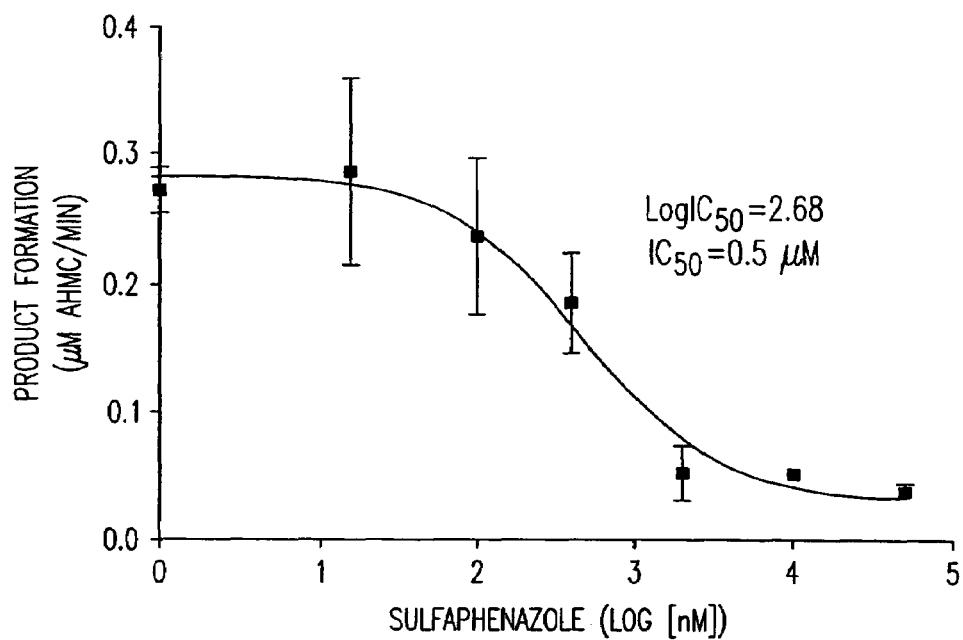
FIG. 5. Effect of sulfaphenazole on AMMC demethylase activity. (A) The rate of AHMC product formation was assessed and the $IC_{50}$ value was calculated. (B) AHMC product formation was measured over 2 hours in baulovirus-infected CYP2D2-specific supersomes in the presence or absence of sulfaphenazole (50 µM) (SUL).
Figure 5B:
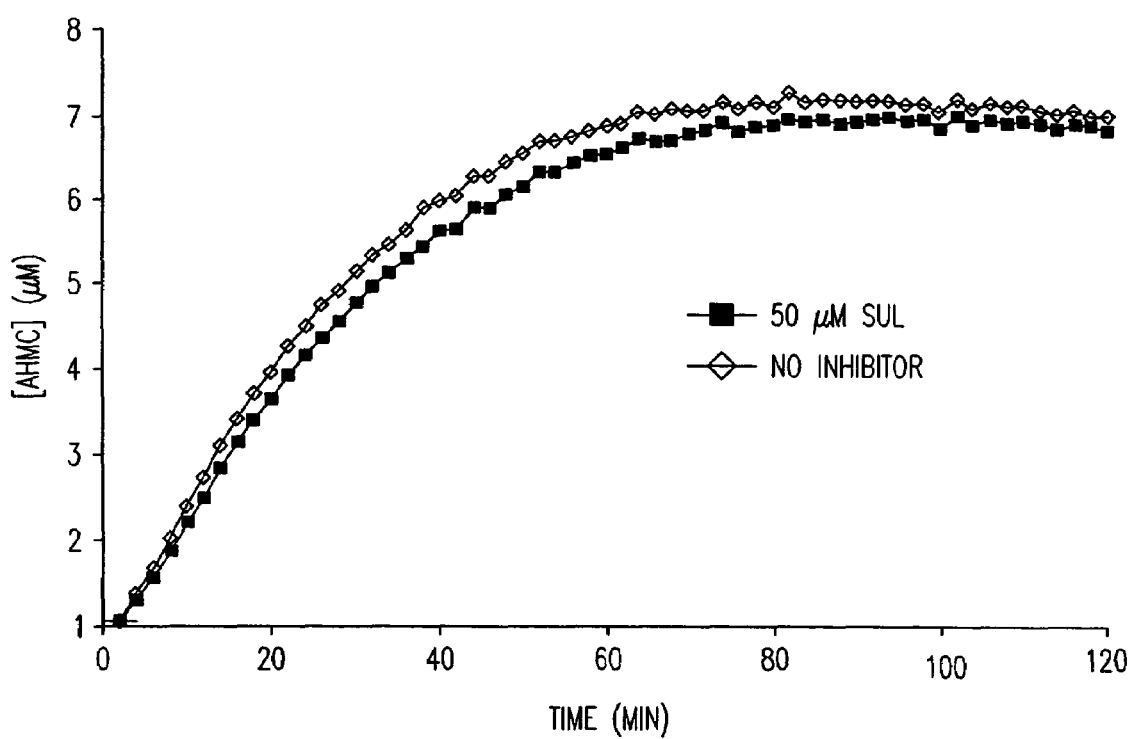

To verify that the phosphoprotein was indeed EF-Tu$_{mt}$, immunoblot analysis of a sample of radiolabeled mitochondrial protein was conducted. Antibody to EF-Tu$_{mt}$ (Woriax et al., 1997) recognized a series of spots that corresponded to the phosphoprotein. To further confirm that the phosphoprotein represented EF-Tu$_{mt}$, mitochondrial extracts were partially purified on a DEAE-Sepharose anion exchange column following a protocol developed for the purification of EF-Tu$_{mt}$ (Woriax et al., 1997). Fractions were analyzed for the presence of EF-Tu$_{mt}$ and for the p46 phosphoprotein. As shown in FIG. 5B, the radiolabeled phosphoprotein (top panel) eluted in exactly the same fractions as EF-Tu$_{mt}$ (bottom panel). Because EF-Tu$_{mt}$ and EF-Ts$_{mt}$ elute as a complex on DEAE-Sepharose, this procedure depends on different biochemical properties than 2D gel electrophoresis (Woriax et al., 1997). It is unlikely that another protein would copurify with EF-Tu in both schemes. Based on these studies, it was concluded that the phosphoprotein is indeed EF-Tu$_{mt}$.

The foregoing observations indicated that EF-Tu$_{mt}$ undergoes phosphorylation in vitro. To ascertain whether EF-Tu$_{mt}$ was endogenously phosphorylated, mitochondria were isolated from heart in the presence of phosphatase inhibitors and subjected to 2D gel electrophoresis and immunodetection of EF-Tu$_{mt}$. The antibody against EF-Tu$_{mt}$ detected two or possibly three spots that differed slightly by isoelectric point. The distribution of these multiple spots is comparable to that seen in the in vitro phosphorylation experiments and most likely represents the addition of acidic phosphate groups. The presence of three spots suggests the existence of at least two phosphorylation sites. These observations provide evidence that EF-Tu$_{mt}$ is phosphorylated in vivo, even in control hearts. It also raises the possibility that the in vitro phosphorylation that is increased after ischemia could represent "back-phosphorylation" of available unphosphorylated sites, and that in control and preconditioned hearts, EF-Tu$_{mt}$ could actually be highly phosphorylated (thereby leaving few sites available for the incorporation of radioactive phosphate in the in vitro reaction).

Mitochondria were fractionated to determine the submitochondrial localization of the 46 kDa phosphoprotein and to compare this to the distribution of EF-Tu$_{mt}$. The majority of the phosphoprotein was found in the matrix but a portion was found associated with the inner membrane. This distribution was identical to that observed for EF-Tu$_{mt}$. The purity of submitochondrial fractions was also determined. As analyzed by Western blots, an inner membrane component, the Rieske iron-sulfur protein (FeS), was found to be essentially absent from matrix whereas hsp60, a matrix protein, contaminated the inner membrane fraction to some degree. The distribution of EF-Tu$_{mt}$ was comparable to hsp60, indicating that it is likely to reside in the matrix, or is due to reversible association with the membrane. It is interesting to note, however, that EF-Ts$_{mt}$, which is also detected by the antibody, is only detected in the matrix fraction. Amino acid hydrolysis demonstrated that EF-Tu$_{mt}$ is phosphorylated on serine.

Phosphorylation of EF-Tu in prokaryotes inhibits protein translation. It was possible that the same might be true for eukaryotic EF-Tu. If so, then inhibition of mitochondrial protein synthesis would be expected to reproduce the effects of EF-Tu$_{mt}$ phosphorylation. To test this possibility, hearts were pretreated with CAP, a potent inhibitor of mitochondrial protein synthesis, and the effects on infarct size after ischemia and reperfusion, were examined. CAP treatment reduced the infarct size from 64.1 (±4.1) to 43.1 (±6.4) (mean±SEM) and CK release, after global ischemia suggesting that inhibition of mitochondrial protein synthesis may be cardioprotective. CAP administered in the last 15 minutes of the 2 hour reperfusion was not protective (infarct size 69.2±5.7).

CAP treatment also resulted in deceased immunodetection of the mitochondrial-encoded protein cytochrome oxidase subunit I while nuclear encoded mitochondrial proteins such as VDAC, ANT, Hsp60, FeS (Rieske), and cytochrome oxidase IV remained unchanged (data not shown). CAP infusion for as little as 15 minutes was sufficient to cause near-complete loss of the mitochondrial-encoded protein cytochrome oxidase I. This suggests that turnover of some mitochondrial-encoded proteins in the heart is extremely rapid.

Discussion

A number of protein kinases are activated during ischemia, reperfusion, or preconditioning, and at least two of these are believed to translocate to the mitochondria. It is possible that either a small molecule or a cytosolic kinase could transmit a signal to the mitochondria to stimulate phosphorylation of EF-Tu$_{mt}$. In fact, cytosol from normal hearts suppressed phosphorylation of EF-Tu$_{mt}$, whereas the absence of any cytosol, or the presence of ischemic cytosol, favors phosphorylation (see above). Because the experiments described above were performed in the presence of phosphatase inhibitors, this could represent a balance between kinases and phosphatases that are differentially regulated by cytosolic factors.

Because phosphorylation of EF-Tu$_{mt}$ is increased in response to ischemia, the effect of ischemic preconditioning on EF-Tu$_{mt}$ phosphorylation was determined. To measure the activity of the endogenous mitochondrial kinase with respect to EF-Tu$_{mt}$ phosphorylation, mitochondria were isolated from control, ischemic, and preconditioned hearts. The purified mitochondria were incubated with [γ-$^{32}$P]ATP in the absence of cytosol. Preconditioning diminished the amount of phosphorylation seen at 15 minutes of reperfusion. As previously noted, mitochondria incubated in buffer only demonstrated a basal level of phosphorylation of EF-Tu$_{mt}$, whereas cytosol from control or preconditioned hearts suppressed phosphorylation. Cytosol from ischemic hearts, or mitochondria prepared from ischemic hearts, stimulated phosphorylation of EF-Tu$_{mt}$. These observations suggest that the cytosol of normal, metabolically active cardiomyocytes is effective in regulating the phosphorylation of EF-TU$_{mt}$, but that the cytosol of ischemic or metabolically inhibited cells has lost the ability to regulate this phosphorylation process. An alternative interpretation is that there is a factor present in cytosols from ischemic hearts that stimulates phosphorylation of EF-Tu$_{mt}$. The altered phosphorylation of EF-Tu$_{mt}$ in ischemic versus control cytosols is unlikely to be due to dilution of [γ-$^{32}$P]ATP in different concentrations of cytosolic ATP nor due to altered ATP transport through the adenine nucleotide translocator, as other phosphoprotein bands showed similar levels of phosphorylation under all conditions. This phosphorylation was increased in mitochondria from hearts subjected to ischemia and 15 minutes of reperfusion, but the level decreased to baseline if reperfusion was extended to 90 minutes. These results indicate that phosphorylation of EF-Tu$_{mt}$ is regulated by ischemia and by preconditioning.

Members of the MAPK family have been implicated in ischemic injury (He et al., 1999; Raines et al., 1999; Wang et al., 1998) and in preconditioning (Weinbrenner et al., 1997; Maulik et al., 1998; Haq et al., 1998). However, immunodepletion of JNK and p38 did not affect the phosphorylation of EF-Tu$_{mt}$, suggesting that this may be regulated by other kinase pathways. The finding that genistein inhibited phosphorylation and that EF-Tu$_{mt}$ is phosphorylated on serine suggests that the signal transduction pathway responsible for EF-Tu$_{mt}$ phosphorylation involves both a tyrosine kinase and a serine/threonine kinase.

What is the significance of EF-Tu$_{mt}$ phosphorylation? Mitochondria contain an organelle-specific protein-synthesizing system that is essential for the synthesis of the 13 polypeptides encoded by the mitochondrial genome. All of the protein products of this system are components of the electron transport complexes and the F$_0$F$_1$ ATP synthase located in the inner membrane of mitochondria. Previous investigations have identified alterations in the function of electron transport complexes I and IV, which include mitochondrial encoded subunits, whereas complex II, which only contains nuclear-encoded subunits, is unaffected.

It was surprising that the major target of phosphorylation was EF-Tu$_{mt}$. EF-Tu is a GTPase that serves to bind aa-tRNAs and bring them to the ribosome. In bacteria, phosphorylation of EF-Tu on threonine 382 has been shown to prevent ternary complex formation (Lippmann et al., 1993; Kraal et al., 1999). This Thr residue is highly conserved in EF-Tu and is present in the mammalian mitochondrial factors whose sequences are currently available. This residue is, therefore, likely to be a Thr in rabbit EF-Tu$_{mt}$. The site of serine phosphorylation in rabbit EF-Tu$_{mt}$ remains to be determined. In addition, the number of phosphorylation sites is undetermined. The MALDI spectra were identical for all three spots that differed by isoelectric points, which is consistent with two phosphorylation sites. However, it is also possible that glycosylation or minor proteolysis at the N- or C-terminus could give rise to a spot with a shifted pI without a detectable difference in molecular mass. EF-Tu$_{mt}$ had not previously been reported to be phosphorylated and further studies will be required to determine the effect of this modification on its activity in protein synthesis. The fact that EF-Tu$_{mt}$ phosphorylation is enhanced in ischemic hearts compared with control or preconditioned hearts leads indicates that the phosphorylation carries some physiological significance. It is attractive to speculate that EF-Tu$_{mt}$ phosphorylation leads to inactivation of mitochondrial protein synthesis with consequent loss of mitochondrial subunits essential for function of complexes I and IV. This may explain the cardioprotective effects of CAP treatment, particularly if complex I participates in superoxide production during reperfusion. In addition, inhibition of mitochondrial protein synthesis may be energy-sparing, allowing the utilization of limited ATP for more essential needs.

The abundance of EF-Tu$_{mt}$ has been shown to increase in tumor cells (Wells et al., 1995) and nearly disappears in pacing-induced heart failure, along with a number of other mitochondrial proteins (Heinke et al., 1998). *Escherichia coli* EF-Tu has also been reported to function as a chaperone (Kudlicki et al., 1997). It is possible that this activity is regulated by phosphorylation. EF-Tu$_{mt}$ may play a role analogous to the heat shock proteins by participating in mitochondrial protein refolding after ischemic injury.

EXAMPLE II

Methods

Langendorff Heart Perfusions.

All procedures were approved by the Animal Care and Use Committee at The Scripps Research Institute (TSRI). Rat hearts were perfused in Langendorff mode with Krebs-Ringer buffer as in Example I. CAP (300 µM) (Calbiochem, San Diego, Calif.), gentamicin sulfate (50 mg/ml) (Sigma, St. Louis, Mo.), ketoconazole (7.5 µM), sulfaphenazole (10 to 300 µm) (Sigma, St. Louis, Mo.) or cimetidine (200 to 600 µM) was added to the perfusion buffer 20 minutes before ischemia or upon reperfusion. No-flow ischemia was maintained for 30 minutes and reperfusion was accomplished by restoring flow for 15 minutes for creatine kinase (CK) release determination and dihydroethidium (DHE) staining, or 120 minutes for infarct size determination by triphenyl tetrazolium chloride (TTC) staining. Measurement of CK activity was performed using the CK EC 2.7.3.2 UV-Test kit (Sigma) as per the manufacturer's instructions. The measurement of infarct size after TTC staining was performed as described in Example 1.

Rabbit Circumflex Occlusion.

Twelve New Zealand white rabbits (2.8 to 3.9 kg) were randomized to receive an intravenous bolus of CAP (20 mg/kg in sterile saline) or vehicle (no drug) 30 minutes before regional ischemia. Animals were mechanically ventilated with room air via a tracheostomy, and the heart was exposed by a median sternotomy. A suture ligature was passed around the circumflex coronary artery so it could be snare-occluded and reperfused as described in Gottlieb et al. (1994). Ischemia was induced by snare occlusion and confirmed by visual inspection. After 30 minutes of ischemia, the ligature was released and the heart was reperfused for 4 hours. The heart was then rapidly excised, and the normal area of perfusion marked by infusion of acridine orange. The heart was frozen and assessed for infarct size the following day using TTC staining. Infarct size as a percentage of the area at risk (demarcated by acridine orange staining) was determined by an observer blinded to the treatment status of the hearts.

Measurement of Superoxide Production.

Superoxide generation was assessed via the conversion of dihydroethidium (DHE) to ethidium as described in Miller et al. (1998). Heart slices (1 mm thick) were stained in 2 mM DHE (Molecular Probes, Eugene, Oreg.) in PBS in the dark at 37° C. for 20 minutes. Sections imaged on an ultraviolet transilluminator (Fisher Scientific) with a Kodak DC120 digital camera (Kodak) using Kodak Digital Science 1D software (Kodak) were saved as TIFF files and analyzed using Adobe Photoshop 5.5. The relative fluorescence intensity reflecting superoxide production was quantified as the ratio of fluorescent (white) pixels to the total heart area.

Preparation of Mitochondria and Measurement of Oxygen Consumption.

Hearts were rapidly minced in ice-cold MSE buffer (in mmol/L, mannitol 220, sucrose 70, EGTA 2, MOPS 5 (pH 7.4), and taurine 2 supplemented with 0.2% fatty acid-free bovine serum albumin (BSA)). Heart tissue was homogenized in MSE with a Polytron type tissue grinder at 11,000 rpm for 2.5 seconds followed by 2 quick strokes at 500 rpm with a loose fit Potter-Elvehjem tissue grinder. The homogenate was centrifuged at 500 g twice for 5 minutes, saving the supernatant. Mitochondria were pelleted from the supernatant by centrifugation at 3000 g twice, and the pellet was rinsed with MSE buffer. The supernatant was saved as crude cytosol. The final pellet was rinsed and resuspended in 50 µl Incubation Medium (in mmol/L, mannitol 220, sucrose 70, EGTA 1, MOPS 5 (pH 7.4), taurine 2, $MgCl_2$ 10, and $KH_2PO_4$ 5, supplemented with 0.2% fatty acid-free BSA) (Scholte et al., 1997). Mitochondria were incubated for 15 minutes on wet ice and protein concentration was determined with BSA as a standard by a Bradford assay. All work was performed on wet ice at 0° C.

Measurement of Respiration in Mitochondria from Mouse or Rat Hearts.

Oxygen consumption was measured at 30° C. with a Clark type oxygen electrode (Instech) in 600 µl KCl respiration buffer (in mmol/L: KCl 140, EGTA 1, MOPS 10 (pH 7.4), $MgCl_2$ 10, and $KH_2PO_4$ 5, supplemented with 0.2% fatty acid-free BSA) (Scholte et al., 1997; Chance et al., 1961; McKee et al., 1990). Complex II activity was measured using 200 µg mitochondria with succinate, 5 mM, as a substrate. Complex IV activity was measured using 150 µg mitochondria with TMPD, 0.4 mM and ascorbate, 1 mM, as a substrate. For each complex the ADP-stimulated respiration rate (state 3) was measured after the addition of 2 mM ADP; the ADP-independent respiration rate, oligomycin-insensitive (state 4) was measured after the addition of 2 µM oligomycin; and the maximal respiration rate was measured after uncoupling the mitochondria with 2 µM FCCP. Rates were calculated as nA $O_2$/min/mg protein after subtracting the rate that was insensitive to the inhibitors antimycin A, 1 µM, for complex III, and KCN, 1 mM, for complex IV. As a measure of mitochondrial integrity, the respiratory control ratio (RCR) state 3 divided by state 4 was calculated.

Immunoblotting for Mitochondrial Proteins.

Mitochondria (50 µg) were resolved by SDS-PAGE and transferred to PVDF nylon membranes. Membranes were probed for ND3 with antibodies kindly provided by Dr. Akemi Matsuno-Yagi, The Scripps Research Institute, and for cytochrome oxidase subunit I (Molecular Probes, Eugene, Oreg.). Detection was performed with ECL (Amersham, Piscataway, N.J.). Non-saturated autoradiographs were quantitated with Scion/NIH Image.

Measurement of Cytochrome P450 Activity in Heart Microsomes.

Immediately following ischemia/reperfusion in the presence or absence of CAP (300 µM), the rat hearts were homogenized in a post-mounted rotor-stator tissue homogenizer in KCl buffer (0.15 M, pH 7.4). Microsomes were isolated from rat livers (Sprague-Dawley, male, 6-8 weeks) by differential centrifugation as described by Walles and coworkers (2001). Homogenized tissue was centrifuged at 11,000 g for 30 minutes at 4° C. The supernatant was further centrifuged at 170,000 g for 60 minutes at 4° C. The resulting pellet was resuspended in KCl buffer and centrifuged at 200,000 g for 40 minutes at 4° C. The microsomal fraction was then transferred into Tris-sucrose buffer (0.25 M sucrose, 20 mM Tris buffer, 5 mM EDTA). Protein concentrations were determined by bicinchoninic acid micro assay (Pierce). Microsomal solutions were aliquoted and stored at −80° C. until further use.

Fluorometric Cytochrome P450 Assay.

Assays were carried out in parallel at 37° C. in fluorescence detector microtiter plates (96 well). CYP2D2 supersomes, substrates (AMMC), product standard 3-[2-(N,N-diethyl-N-methylamino)ethyl]-7-hydroxy-4-methylcoumarin (AMHC), and the NADPH generating system were obtained from BD Gentest (Woburn, Mass.). Reaction components were pre-warmed to 37° C. The assay was initiated by addition of the NADPH-regenerating system to substrate concentrations selected to give linear time-course profiles (AMMC, 30 μM) and rat liver microsomal protein (10 mg/ml) isolated as described above in phosphate buffer (50 mM, pH 7.4) (final organic co-solvent concentration, 0.1% acetonitrile) in the presence or absence of sulphaphenazole (50 μM AMMC). Reaction progression was followed by continuously monitoring AHMC formation ($\lambda_{ex}$=390 nm and $\lambda_{em}$=460 nm) using a SPECTRAmax™ GEMINI dual-scanning microplate spectrofluorometer for 1 hour at 37° C. The residual absorption due to NADPH was compensated for throughout the analysis. Each assay was performed in at least triplicate. Reaction progress was followed for no more than 10% of total reaction during which time the reaction rate was linear ($r^2$>0.985). These linear initial changes in residual fluorescence emission were converted to concentration and hence rates of product formation by comparison to standard curves. IC50 determination for AHMC was performed using Graphpad Prism® software (San Diego, Calif.). For cardiac microsomes, the inhibition by chloramphenicol was calculated, as a percent, by a comparison of the initial rates of AHMC formation between the cardiac microsomal preparations obtained from the chloramphenicol treated and untreated groups.

Statistical Analysis.

Statistical analysis was performed between groups by ANOVA using GraphPad InState 4.10 software (San Diego, Calif.). A p value less than 0.05 was considered significant.

Results

Figures 1, 2A:
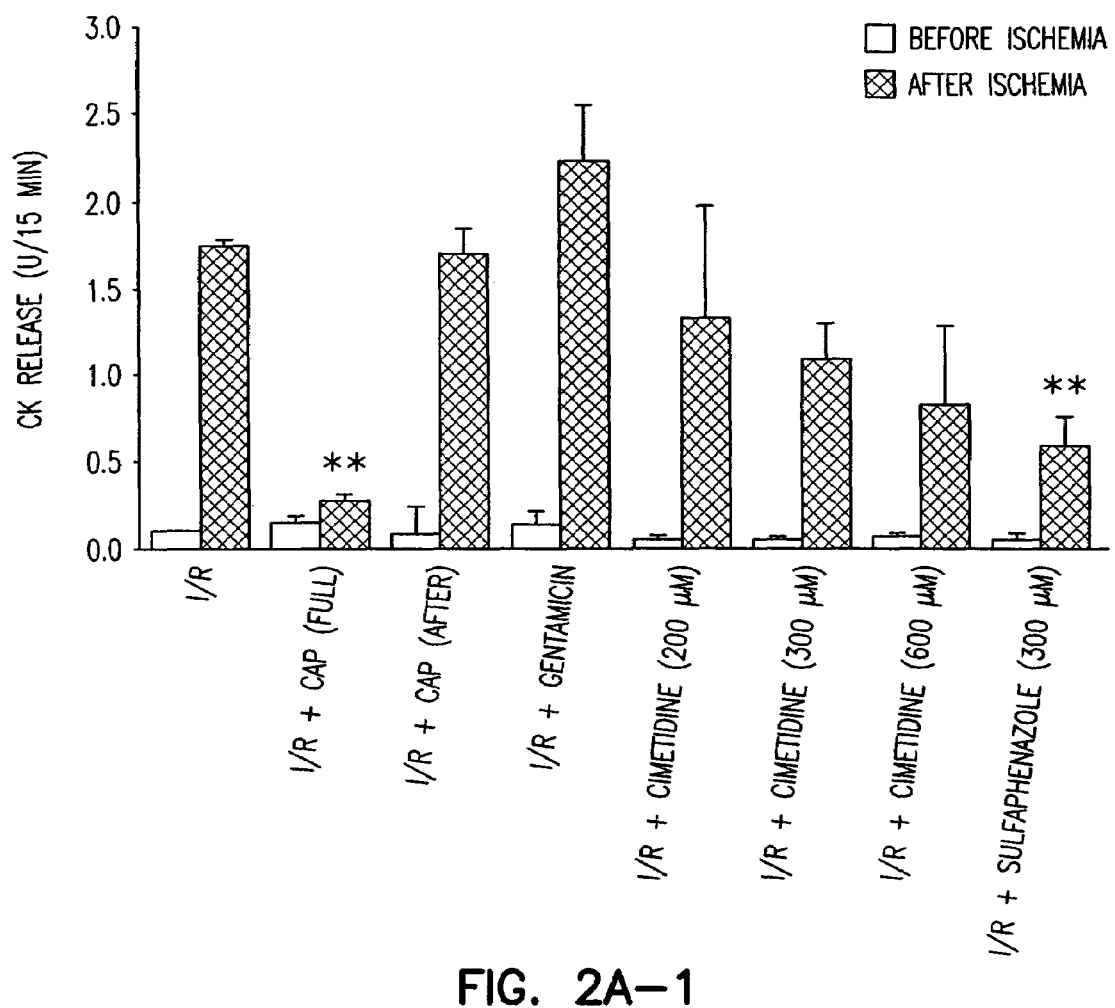

The effects of CAP administration on CK release, coronary flow and infarct size during reperfusion were assessed in isolated rat hearts perfused in Langendorff mode. Treatment with CAP (300 μm) before and after global no-flow ischemia (I/R+CAP) resulted in a significant reduction in infarct size from 43.2±3.2% (SEM) (n=16) (untreated) to 16.0±3.6% (n=5, p<0.005) (treated), respectively (FIG. 2A). CAP administered prior to ischemia substantially decreased the amount of CK released after ischemia from 2.25 U/15 min±0.28 (SEM) (n=16) in untreated hearts to 0.27±0.13 (n=5, p<0.01). Effects on coronary flow paralleled those for cardioprotection. Gentamicin, a structurally unrelated antibiotic, was not cardioprotective in this model, arguing against a possible antimicrobial effect of CAP. Furthermore, administration of chloramphenicol immediately after ischemia also substantially reduced infarct size (21.7%±2.7, n=5 versus 43.2%, p<0.01), suggesting that reperfusion injury is a major determinant of tissue damage in this model.

Figures 2, 2A:
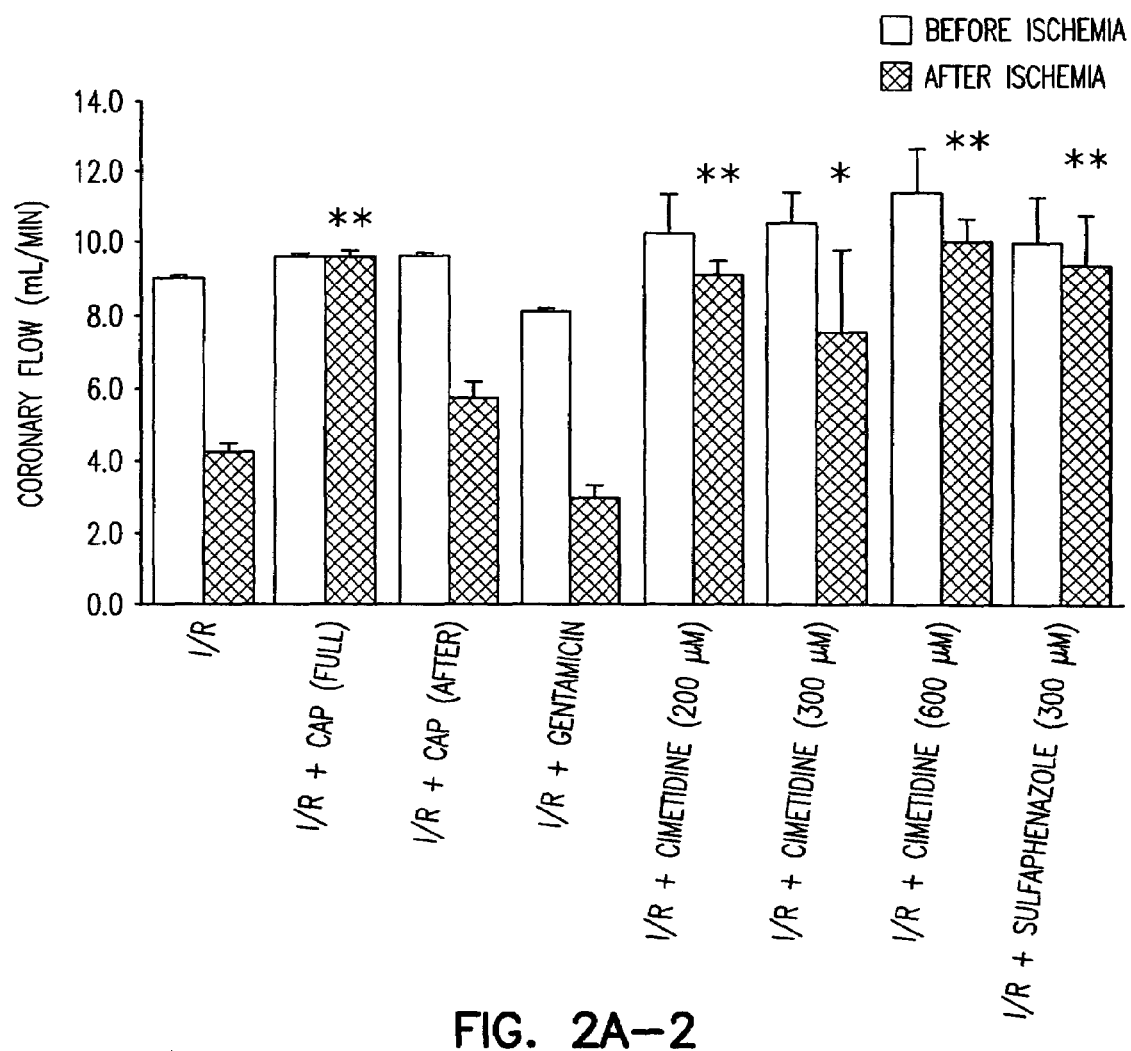
FIG. 2. Reduced infarcts in chloramphenicol-, cimetidine- and sulfaphenazole-treated hearts after ischemia/reperfusion (I/R). Adult rat hearts were perfused in Langendorff mode for 20 minutes, then subjected to 30 minutes no-flow ischemia followed by a 2 hour reperfusion. Chloramphenicol (CAP), gentamicin, cimetidine, or sulfaphenazole was added for the entire procedure (Full) or immediately after ischemia for reperfusion (CAP-After). (A) After 2 hours of reperfusion, hearts were frozen and assessed for infarct size using TTC. Coronary effluent was collected for 15 minutes immediately before and after ischemia and assessed for CK release. Error bars denote SEM. * indicates p<0.01, and ** indicates P<0.001 (comparison to I/R). (B) Representative heart sections stained with TTC for each treatment.
Figures 2, 2A, 3:
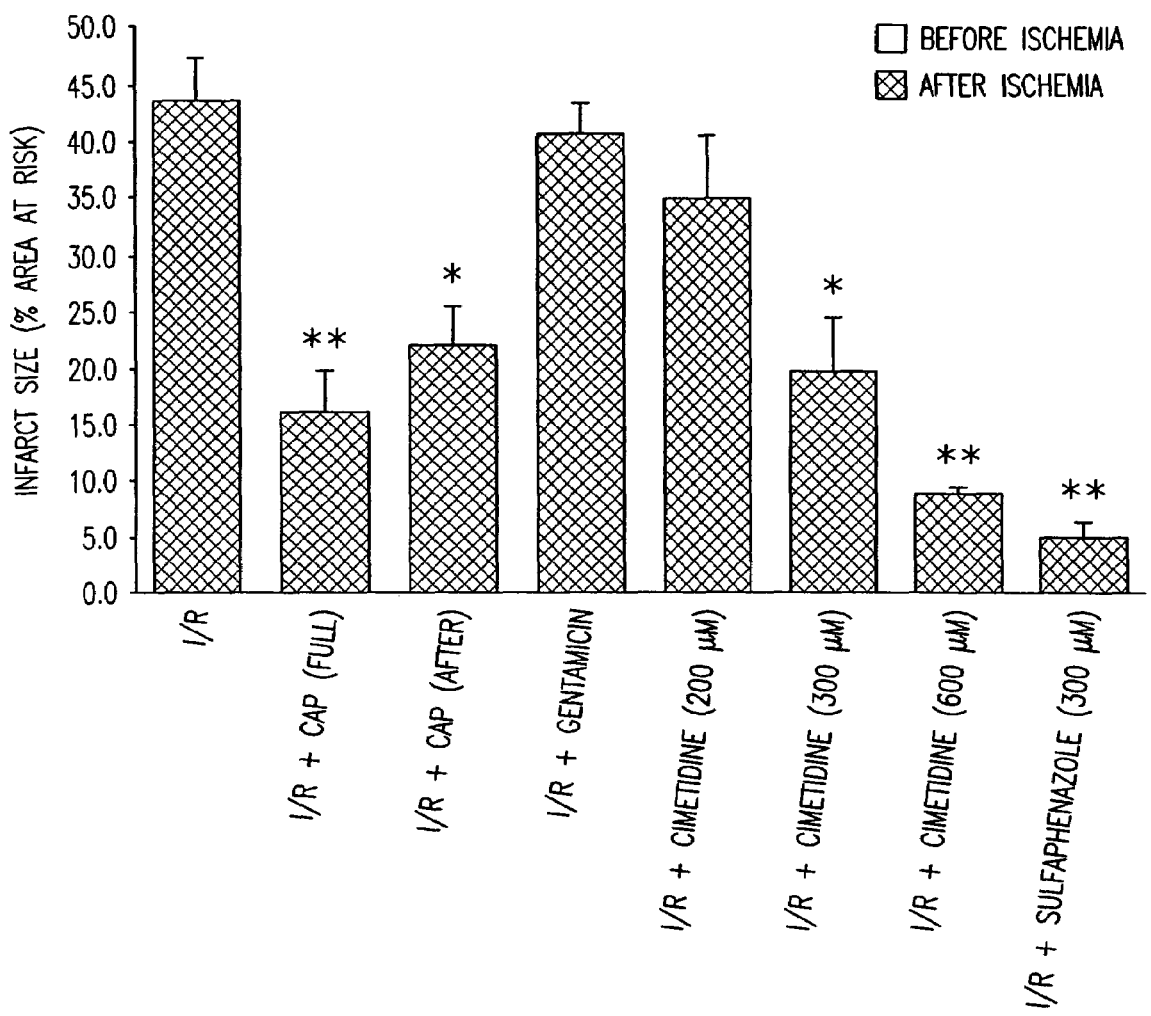
FIG. 3. Chloramphenicol significantly reduces infarct size and suppresses post-ischemic hypotension following circumflex coronary artery occlusion in rabbits. Rabbits were injected with or without CAP (20 mg/kg) 30 minutes before the induction of 30 minutes of ischemia (coronary occlusion) followed by 4 hours reperfusion. (A) At 4 hours, hearts were removed, immediately frozen and blindly assessed for infarct size. The decrease in left ventricular pressure from baseline was assessed after ischemia. The error bars represent the mean and standard error (n=6). The asterisk represents a p value<0.05. (B) Rat hearts were perfused in Langendorff mode with or without CAP (100 µg/ml) for 15 minutes and then subjected to 20 minutes ischemia and 15 minutes reperfusion with the same buffer. Superoxide levels were assessed by measuring DHE conversion to ethidium. The asterisk represents a p value<0.05. Error bars represent the standard error for ischemia/reperfusion (n=5), ischemia/reperfusion+CAP (100 µg/ml) (n=4).

Given that both mitochondria and cytochrome P450 monooxygenases are known to generate ROS under certain conditions, the mechanism of cardioprotection by CAP may be due to the known inhibitory potential of CAP on both mitochondrial protein synthesis as well as cytochrome P450 isozymes (Kraner et al., 1994). Mitochondrial protein synthesis and activity were determined by Western blotting, mitochondrial oxygen consumption and blue native PAGE (data not shown), respectively, to assess the effects of chloramphenicol on mitochondrial function (FIG. 2 and Table 2). The latter experiments suggested that perfusion with CAP for 30 minutes was not sufficient to alter the levels of mitochondrial-encoded proteins or to affect respiratory chain activity, suggesting that CAP did not have an appreciable effect on mitochondria.

TABLE 2

| | Complex I (n Atoms O/min/mg) | | Complex II (n Atoms O/min/mg) | | Complex IV (n Atoms O/min/mg) | |
|---|---|---|---|---|---|---|
| | State 3 | State 4 | State 3 | State 4 | State 3 | State 4 |
| −CAP | 158.57 ± 32 | 13.74 ± 6.33 | 85.47 ± 22.2 | 21.70 ± 5.89 | 209.85 ± 40 | 113.99 ± 21 |
| +CAP | 162.99 ± 31 | 12.09 ± 4.59 | 83.58 ± 14.4 | 23.04 ± 7.32 | 201.09 ± 23 | 116.89 ± 23 |

⁺Rat hearts were perfused with or without chloramphenicol for 30 minutes, then mitochondria were isolated and oxygen consumption was assessed.

To assess if CAP administration during I/R in the Langendorff model vide supra is inactivating cardiac activity, cardiac microsomes from pooled hearts (2 per group) were isolated immediately after reperfusion in the presence and absence of CAP and cytochrome P450 activity measured. Cytochrome P450 activity was determined for the NADPH-dependent demethylation reaction of the fluorescent substrate 3-[2-(N,N-diethyl-N-methylamino)ethyl]-7-methoxy-4-methylcoumarin (AMMC, 100 μM), a substrate for the cytochrome P450 2D in rats (and P450 2C in humans) superfamily in rats and 2C superfamily in humans. Cytochrome P450 AMMC O-demethylase activity was inhibited by 95% in the microsome prepared from CAP-treated rat hearts.

Figure 2B:
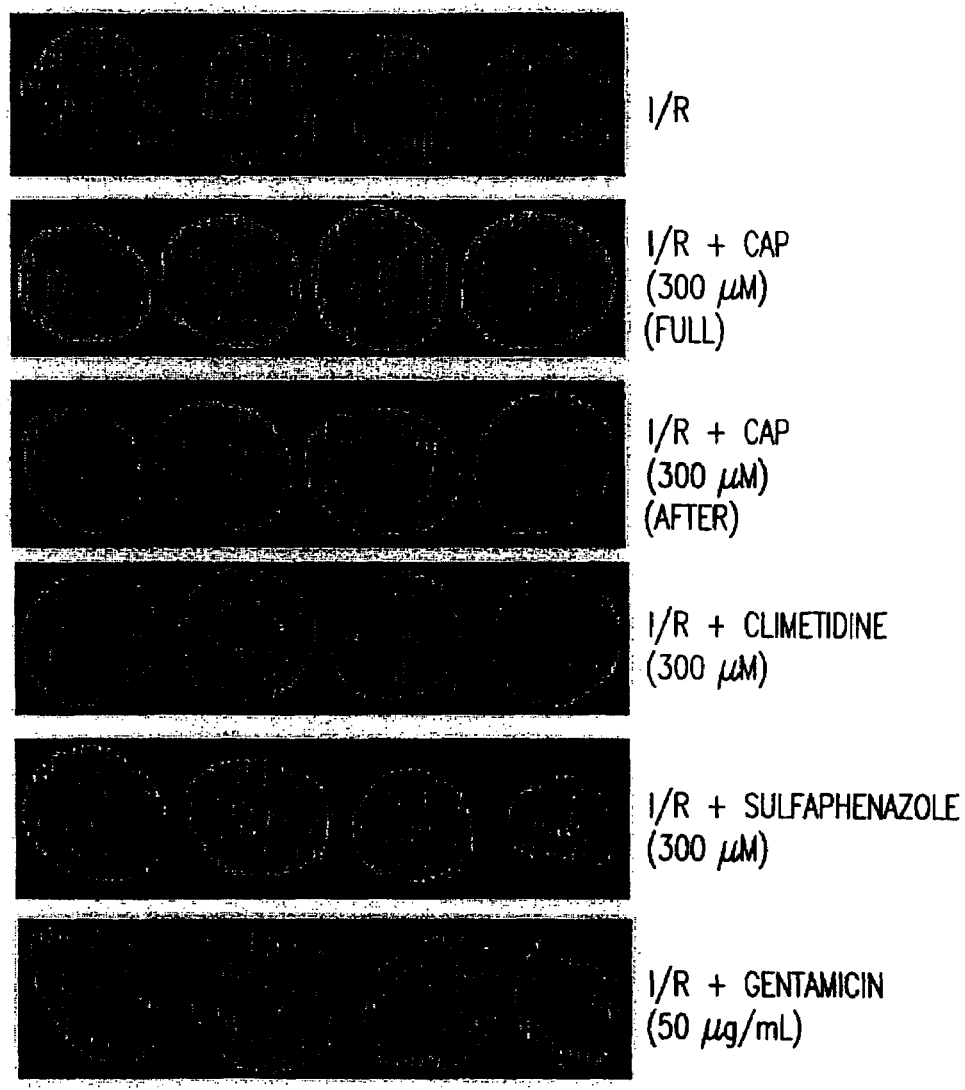
Figure 2C:
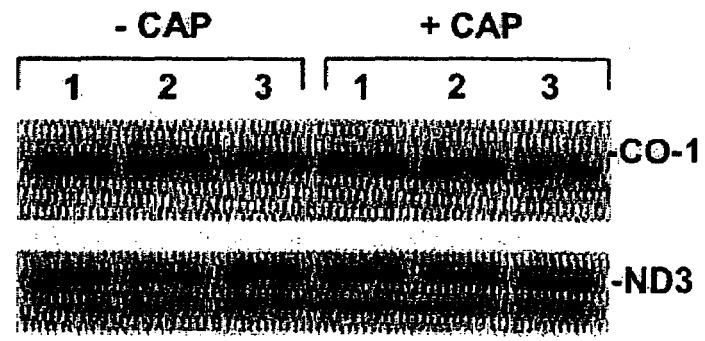

To ascertain whether the cardioprotective effect of CAP was due to the inhibition of cytochrome P450, cimetidine, a cytochrome P450 inhibitor that does not affect mitochondrial protein synthesis was studied in the Langendorff perfusion model. Cimetidine (200-600 μM) conferred a dose-dependent reduction in infarct size (FIGS. 2A-B). Parallel to its effects on infarct size, cimetidine also reduced CK release (FIG. 2A). Post-ischemic coronary flow was also enhanced in treated hearts. Since CAP and cimetidine are both known to inhibit the cytochrome P450 2C subfamily (Kraner et al., 1994; Rendic et al., 1997), the selective cytochrome P450 2C inhibitor, sulfaphenazole, was tested. Sulfaphenazole (10 μM and 300 μM) treatment resulted in a significant reduction in CK release and infarct size following 2 hours reperfusion, suggesting that the cytochrome P450 2C family may play a significant role in reperfusion injury.

Sulfaphenazole, while being a fairly selective inhibitor of human CYP2C9, is not known to be an inhibitor of rodent P450 isozymes. Therefore, after observing the dose-dependent protection by sulfaphenazole against ischemia-reperfusion injury, inhibition of rodent P450 isozyme activity by sulfaphenazole was examined. The effect of sulfaphenazole concentration on rat hepatic microsome, isozyme-mediated modification was investigated with the fluorogenic substrate AMMC, which is a selective substrate for CYP2D2 in rat and CYP2D6 in humans. Sulfaphenazole was found to inhibit AMMC demethylation in rat liver microsomes ($IC_{50}$ 0.5 μM) (FIG. 5A). To determine whether CYP2D2 is the AMMC demethylase that is inhibited by sulfaphenazole, the effect of sulfaphenazole (50 μM) on AMMC demethylase activity was assessed using CYP2D2 supersomes (microsomes isolated from baculovirus-infected insect cells that specifically express CYP2D2). Interestingly, sulfaphenazole did not appear to significantly inhibit CYP2D2 activity, suggesting that sulfaphenazole is inhibiting a as yet unidentified CYP AMMC demethylase (FIG. 5B).

Figure 3A:
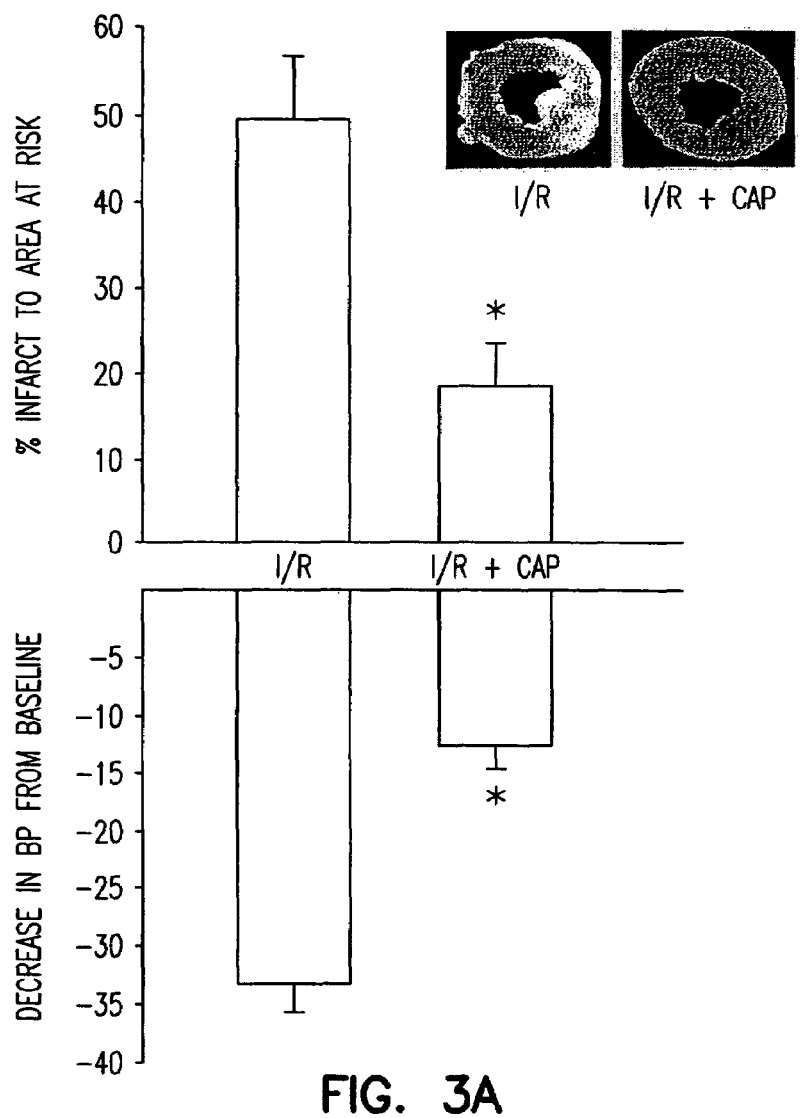

The observed cardioprotective effect of CAP is not model-specific. In addition to the Langendorff model, the protective effect of CAP was studied in a rabbit model of circumflex coronary artery occlusion. Rabbits were administered either CAP (20 mg/kg i.v. in saline) or no drug 30 minutes before snare-occlusion of the coronary artery for 30 minutes, followed by 4 hours of reperfusion (FIG. 3A). The volume of the area at risk did not differ between the two groups (not shown). However, similar to the Langendorff model, CAP administration significantly reduced infarct size: 49.3% of the area at risk ±17.7 (untreated) versus 18.3%±12.1 (CAP treated) (n=6, p<0.05) (FIG. 3A). Post-ischemic hypotension was also diminished in the drug-treated rabbits (−34.2 mm $H_2O$±2.3 versus −13.3±2.2, n=6, p<0.05) (FIG. 3A).

Figure 3B:
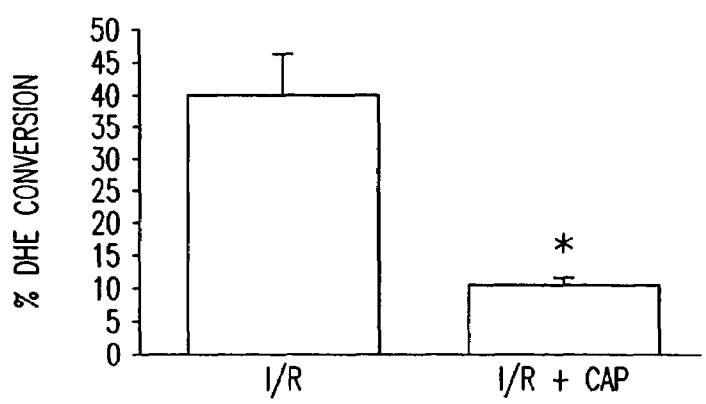
Figure 4A:
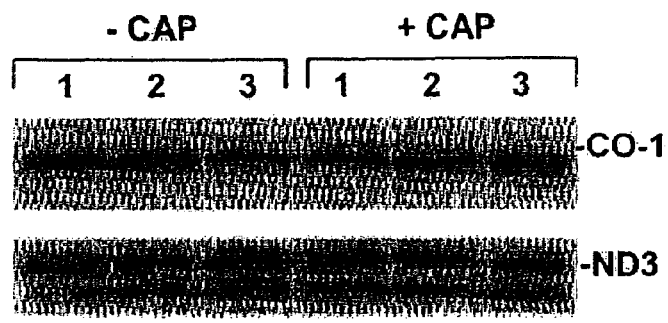
FIG. 4. Effect of chloramphenical infusion on mitochondria and CYP activity. (A) Mitochondria isolated from hearts perfused with or without chloramphenicol were assessed for expression levels of mitochondrial genome-encoded proteins cytochrome oxidase subunit 1 (CO-1) and Complex 1 subunit 3 (ND3). (B) Mitochondrial respiration was measured by polarography. State 3 and State 4 respiration are shown for palmitoylcarnitine (Complex 1 substrate), succinate (Complex II substrate), and TMPD/ascorbate (Complex IV substrate). Error bars represent standard deviation. (C) Cardiac microsomes were prepared from hearts perfused with or without chloramphenicol, and CYP activity was measured as the NADPH-dependent demethylation reaction of AMMC.
Figure 4B:
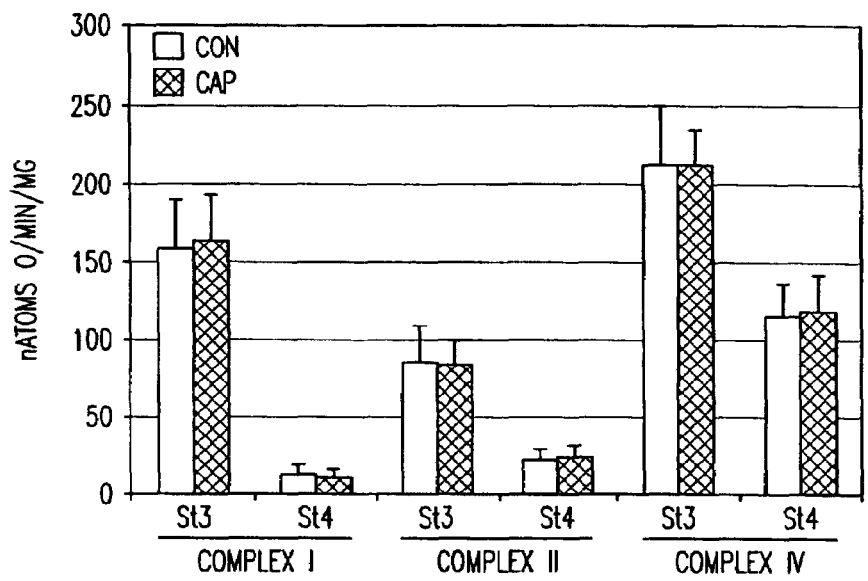
Figure 4C:
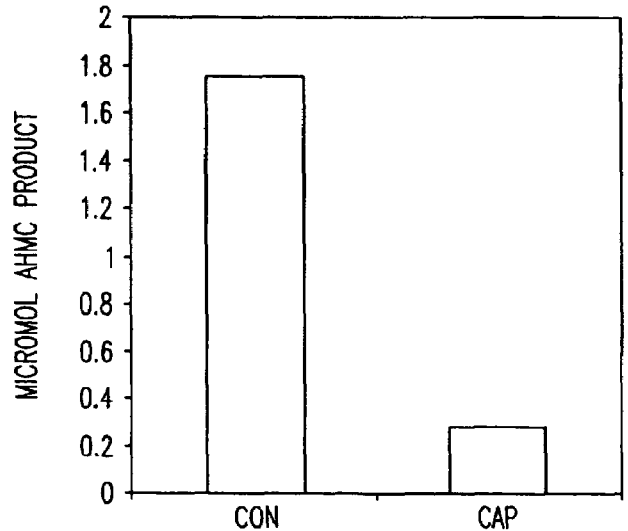

Ischemia/reperfusion injury is known to lead to elevated production of ROS, such as superoxide anion ($O_2^{•-}$), hydrogen peroxide ($H_2O_2$), singlet molecular oxygen ($^1O_2^*$) and hydroxyl radical ($HO^{108}$ •). To assess to what extent the cardioprotective effect of CAP could be attributed to a reduction in the production of ROS, $O_2^{•-}$ generation was measured in heart slices obtained after 15 minutes of reperfusion (FIG. 3B). The oxidation of dihydroethidium (DHE) to ethidium, a quantifiable chemical marker of superoxide anion production, was reduced approximately three-fold in CAP treated hearts versus ischemia/reperfusion without drug (33.6%±5.0 versus 10.5±1.6, p<0.05, n=4).

Discussion

A recent RT-PCR analysis of explanted human heart tissue revealed the presence of CYP 1A1, 2B6/7, 2C8-19, 2D6, 2E1, and 4B1 (Thum et al., 2000) as well as cytochrome P450 with arachidonic acid epoxygnease activity, i.e., CYP2J2 (Wu et al., 1996). Moreover, endothelial CYP2C9, which has been reported to metabolize arachidonic acid to epoxyeicosatrienoic acids (EETs), has also been shown to be a functionally significant source of reactive oxygen species in coronary arteries (Fleming et al., 2001). The arachidonic acid metabolizing CYP enzymes that have been linked to prominent roles in vascular regulation are the epoxygenases of the 2 gene family (e.g. 2B, 2C8, 2C9, 2C10, 2J2 in humans; 2C34 in pigs; 2C11, 2C23 and 2J4 in rats) that generate a series of regio- and stereospecific epoxides (11,12-EET, 14,15-EET, 8,9-EET, and 5,6-EET) and the ω-hydroxylases belonging to the CYP 4A family that form HETEs (19-HETE and 20-HETE). Notably, there are some enzymes, e.g. rat CYP 4A2 and 4A3, which are capable of hydroxylation and epoxygenation(Nguyen et al., 1999).

The finding that chloramphenicol and the structural unrelated cytochrome P450 inhibitors cimetidine and sulfaphenazole reduce both infarct size and CK release strongly implicate cytochrome P450 monooxygenases in the heart as being important mediators of myocardial damage after ischemia and reperfusion. Treatment with chloramphenicol, cimetidine or sulfaphenazole was also observed to prevent the associated drop in coronary flow that accompanies ischemia, suggesting that cytochrome P450 inhibition may also attenuate the no-reflow phenomenon that often follows an ischemic insult. Furthermore, chloramphenicol was found to be strongly cardioprotective even when administered at reperfusion, suggesting that reperfusion injury is a major determinant of tissue damage in the Langendorff model. Moreover, the disparity between early CK release and subsequent infarct size suggests that the tissue injury continues to evolve during early reperfusion.

Cytochrome P450 AMMC O-demethylase activity was inhibited by 95% in microsomes prepared from chloramphenicol-treated rat hearts. Sulfaphenazole (10 μM and 300 μM) treatment resulted in a significant reduction in creatine kinase release and infarct size following 2 hours of reperfusion, suggesting that the CYP2C family may play a significant role in reperfusion injury. The finding that an AMMC demethylase activity present in liver and cardiac microsomes was inhibited by sulfaphenazole and chloramphenicol, respectively, suggest that this cytochrome P450 isoform may participate in reperfusion injury.

Vascular tone is regulated by the balance between superoxide anion (vasoconstriction) and nitric oxide (•NO) (vasodilation) (Cai et al., 2000). Superoxide anion reacts with •NO to generate the highly reactive peroxynitrite (ONOO—). Therefore, diminished $O_2^{•-}$ production in cytochrome P450-inhibited hearts would be protective, via a reduction in ONOO— levels and also increase coronary artery dilatation by leading to higher levels of •NO. In support of this notion, increased coronary flow was also observed in hearts treated with chloramphenicol, cimetidine or sulfaphenazole. The results described herein with the selective inhibitor sulfaphenazole suggest that a cytochrome P450 2C9 ortholog may be a key mediator of reperfusion injury.

In humans, cytochrome P450 2C9 is also known as endothelium-derived hyperpolarizing factor (EDHF) synthase due to its ability to convert arachidonic acid to vasoactive eicosanoids (Fisslthaler et al., 1996). Extrapolating from evidence that members of the rat 2C cytochrome P450 superfamily play a key modulatory role in reperfusion injury (Fleming et al., 2001) indicates that ROS production by human cytochrome P450 2C9 may override EDHF-mediated vasodilation.

Eicosanoids can serve as intracellular second messengers for protein kinases. Cytochrome P450 enzyme-generated eicosanoids have been shown to regulate ATP-sensitive $K^+$ channels on the plasma membrane. The possibility therefore exists that cytochrome P450 enzyme-generated eicosanoids could modulate the mitochondrial KATP channel. Arachidonic acid is a substrate for cytochrome P450 epoxygenases as well as cytochrome P450 omega-hydroxylases, and these products have widely different physiologic effects; thus, inhibition of a subset of cytochrome P450 enzymes may have complex consequences. The calcium-independent phospholipase A2 (iPLA2) liberates arachidonic acid, and inhibition of iPLA2 reduces infarct size (Williams et al., 2002). These observations suggest that the participation of cytochrome P450 enzymes in the metabolism of arachidonic acid is of physiologic importance in the myocardium.

Further, cytochrome P450 enzymes affect calcium homeostasis through eicosanoid metabolites and generation of superoxide, which can affect the function of Ca-ATPases, the sodium/calcium exchanger, and other ion channels (Barnes et al., 2000; Zaidi et al., 1999). The pro-apoptotic protein Bik, which shares homology with other Bcl-2 family members only in the BH3 domain (BH3-only), functions at the ER to trigger cytochrome c release from mitochondria (Germain et al., 2002). Therefore, it is likely that cytochrome P450 enzymes regulate apoptosis in certain settings, particularly in the setting of oxidative stress.

The observation that chloramphenicol largely abrogated dihydroethidium conversion suggests that one or more of the heme-containing cytochrome P450 monooxygenase enzymes are the main culprits in the generation of superoxide during reperfusion of the heart. This is surprising considering the relatively low abundance of cytochrome P450 enzymes in heart tissue. However, dysregulated cytochrome P450 activity could lead to mitochondrial damage and secondary production of reactive oxygen species from the electron transfer complexes (Davydov, 2001).

These observations support the hypothesis that cytochrome P450 enzymes in the heart play a significant role in ischemia/reperfusion injury and that inhibition of cytochrome P450 activity has therapeutic value. Moreover, the finding that cytochrome P450 monooxygenases mediate myocardial reperfusion injury has important implications for the treatment of cardiovascular disease. For instance, cigarette smoking upregulates cytochrome P450 enzymes (Rendic et al., 1997) and increases the risk of a fatal myocardial infarction (Weiner et al., 2000), while cholesterol lowering drugs of the statin family are, for the most part, cytochrome P450 inhibitors (Corsini et al. 1999) and reduce cardiovascular risk independently of their cholesterol lowering effects (Comparato et al., 2001). In particular, the HMG-CoA reductase inhibitor fluvastatin is a specific inhibitor of cytochrome P450 2C9 (Scripture et al., 2001), suggesting that cytochrome P450 2C9 inhibition in humans may, in part, be contributing to cardioprotection. Further, cytochrome P450 expression is sexually dimorphic (Park et al., 1999), and may be a reason as to the underlying decreased cardiovascular risk in women.

In summary, the present study suggests that a variety of agents already in clinical use which share the property of inhibiting cytochrome P450 monooxygenases and/or inhibiting enzymes with an open heme pocket, thereby inhibiting the reduction of molecular oxygen by those enzymes, may be of critical and immediate potential for adjuvant therapies to protect organs, including the heart, against the damage that accompanies reperfusion, e.g., to ameliorate reperfusion injury in situations as diverse as acute myocardial infarction, balloon angioplasty, coronary bypass surgery, organ transplantation, and cerebral stroke.

REFERENCES

Baines et al., *J. Cardiovasc. Electrophysiol.*, 10, 741-754 (1999).
Barnes et al., *Mol. Cell. Biochem.*, 203, 1721 (2000)
Becker et al., *Am. J. Physiol.*, 277, H2240-H2246 (1999).
Berg et al., *Atherosclerosis*, 163, 99-104 (2002).
Bolli et al., *J. Clin. Invest.*, 96, 1066-1084 (1995).
Borutaite et al., *Biochim. Biophys. Acta*, 1272, 154-158 (1995).
Boyle et al., *Methods Enzymol.*, 201, 110-149 (1991).
Brasele et al., *Transplantation*, 73, 897-901 (2002).
Caglayan et al., *Pediatr. Surg. Int.*, 18, 255-257 (2002).
Cai et al., *J. Biol. Chem.*, 275, 20308-20314 (2000).
Carroll et al., *Adv. Exp. Med. Biol.*, 407 255-260 (1997).
Cesselli et al., *Circ. Res.*, 89, 279-286 (2001).
Chance, B. & Higihara, B. in *Proceedings on Intracellular Respiration* 3-26 (Congress Biochemistry, Moscow, 1961).
Chen et al., *J. Biol. Chem.*, 276, 30724-30728 (2001).
Chiu et al., *Arch. Surg.*, 101, 478-483 (1970).
Comparato et al., *Nutr. Metab. Cardiovasc. Dis.*, 11, 328-343 (2001).
Comte et al., *Methods Enzymol.*, 55, 98-104 (1979).
Coon et al., *FASEB J.*, 6, 669 (1992).
Corsini et al., *Pharmacol. Ther.*, 84, 413-428 (1999).
Davydov, Trends Biochem Sci. 26:155-160 (2001).
DiLisa et al., *Biochim. Biophys. Acta*, 1366, 69-78 (1998).
DiLisa et al.,*Mol. Cell Biochem.*, 184, 379-391 (1998).
Downey, http://www.usouthal.edu/ishr/help/ttc. Accessed Jul. 29, 2001.
Duan et al., *Can. J. Physiol. Pharmacol.*, 67, 704-709 (1989).
Feldman et al., *Cardiol. Rev.*, 8, 240-247 (2000).
Ferrari, *J. Cardiovasc. Pharmacol.*, 28, S1-10 (1996).
Fisslthaler et al., *Nature*, 401, 493-497 (1999).
Flaherty et al., *Free Radic. Biol. Med.*, 5, 409-419 (1988).
Fleming et al., *Cir. Res.*, 88, 44-51 (2001).
Fleming, *Cir. Res.*, 89, 753-762 (2001).
George et al., *Circ.*, 105, 2416-22 (2002).
Germain et al., *J. Biol. Chem.*, 277, 18053 (2002).
Gottlieb et al., *J. Clin. Invest.*, 94, 1621-1628 (1994).
Gottlieb et al., *J. Clin. Invest.*, 97, 2391-2398 (1996).
Gottlieb et al., *Methods Enzymol.*, 322, 213-221 (2000).
Halestrap et al., *Biochim. Biophy. Acta.*, 1366, 79-94 (1998).
Halmosi et al., *Mol. Pharmacol.*, 59, 1497-1505 (2001).
Halpert et al., *Mol. Pharmacol.*, 23, 445-452 (1983).
Hangaishi et al., *Biochem. Biophys. Res. Commun.*, 285, 1220-1225 (2001).
Haq et al., *FEBS Lett.*, 434, 305-308 (1998).
He et al., *Cell Death Differ.*, 6, 987-991 (1999).
He et al., *Circ. Res.*, 89, 461-467 (2001).
Heinke et al., *Electrophoresis*, 19, 2021-2030 (1998).
Henry et al., *Cardiovasc. Res.*, 32, 930 (1996).
Ito et al., *Clin. Exp. Hypertens.*, 17, 803-816 (1995).
Kavas et al., *Mass Spec. Rev.*, 10, 335-337.
Kay et al., *J. Mol. Cell Cardiol.*, 29, 3399-3411 (1997).
Kelly et al., *J. Biomol. Screen.*, 5, 249-54 (2000).
Kipshidize et al.,*J. Am. Coll. Cardiol.*, 39, 1686-91 (2002).
Kobara et al., *J. Mol. Cell Cardiol.*, 28, 417-428 (1996).
Kraal et al., *Folia Microbiol. (Praha).*, 44, 131-141 (1999).
Kraner et al., *J. Pharmacol. Exp. Ther.*, 270, 1367-1372 (1994).
Kroon et al., *Acta Cardiol.*, 31, 1-13 (1976).
Kudlicki et al., *J. Biol. Chem.*, 272, 32206-32210 (1997).
Kuenzler et al., *J. Pediatr. Surg.*, 37, 457-459 (2002).
Lemaire et al., *Digestive Surgery*, 16, 222-228 (1999).
Lippmann et al., *J. Biol. Chem.*, 268, 601-607 (1993).
Longa et al., *Stroke*, 20, 84-91 (1989).
Loy et al., *J. Neuroscience Methods*, 116, 125-133 (2002).
Mafia et al., *Br. J. Pharmacol.*, 136, 353-60 (2992).
Masimirembwa et al., *Comb. Chem. High Throughtput Screen*, 4, 245-63 (2001).
Masubuchi et al., *Drug Metab.Dispos.*, 26, 338-42 (1998).
Maulik et al., *Am. J. Physiol.*, 275, H1857-H1864 (1998).
McKee et al., *Am. J. Physiol.*, 258, E492-E502 (1990).
Meldrum et al., *J. urology*, 168, 248-252 (2002).
Miller et al., *Circ. Res.*, 82, 1298-1305 (1998).
Miyazawa et al., *J. Lab. Clin. Med.*, 139, 269-278 (2002).
Murry et al., *Circulation*, 74, 1124-1136 (1986).
Nebert et al., *DNA Cell Biol*10, 1 (1991).
Newinan, *Aerosols and the Lung*, Clarke, S. W. and Davia, D. eds., pp. 197-224, Butterworths, London, England (1984).
Nguyen et al., *Am. J. Physiol.*, 276, R1691 (1996).
Nielsen, *APMISJID*-8803400, 97, 447-451 (1989).

Ning et al., *J. Thor. Cardiovascl. Surg.*, 105, 541-549.
Nishimoto et al., *Biochim. Biophys. Acta*, 1576, 225-30 (2002).
Oyekan et al., *Am. J. Physiol.*, 280, H2430 (2002).
Pain et al., *Circ. Res.*, 87, 460-466 (2000).
Park et al., *J. Biol. Chem.*, 274, 7421-7430 (1999).
Piper et al., *J. Mol. Cell Cardiol.*, 17, 885-896 (1985).
Post et al., *Clin. Cardiol.*, 25, 271-8 (2002).
Rendie et al., *Drug Metab. Rev.*, 29, 413-580 (1997).
Roman et al., *Clin. Exp. Pharmacol. Physiol.*, 27, 855-865 (2000).
Scarborough et al., *Drug Metabl. Rev.*, 31, 205 (1996).
Scholte et al., *Molec. Cell. Biochem.*, 174, 61-66 (1997).
Scott et al., *Am. J. Respir. Int. Care Med.*, 165, 1426-1432 (2002).
Scripture et al., *Clin. Pharmacokinet.*, 40, 263-281 (2001).
Scroggins, *J. Infus. Nurs.*, 24, 263-267 (2001).
Singh et al., *Mol. Cell Biochem.*, 147, 77-81 (1995).
Siwik et al., *Circ. Res.*, 85, 147-153 (1999).
Storrie et al., *Methods Enzymol*, 182, 203-225 (1990).
Sun et al., *J. Clin. Invest.*, 97, 562-576 (1996).
Thum et al., *J. Lancet*, 355, 979-983 (2000).
Tsuchida et al., *Circ. Res.*, 75, 576-585 (1994).
VanDeursen et al., *Cell,* 74, 621-31 (1993).
VanDeursen et al., *Proc. Natl. Acad. Sci. USA*, 91, 9091-5 (1994)
Vestal et al., *Rapid Comm. Mass Spec.*, 9, 1044-1050 (2001).
Walles et al., *Drug Metabl. Dispos.*, 29, 761-768 (2001).
Wang et al., *J. Biol. Chem.*, 273, 5423-5426 (1998).
Weinbrenner et al., *J. Mol. Cell Cardiol.*, 29, 2383-2391 (1997).
Weiner et al., *Isr. Med. Assoc.*, J2, 446-449 (2000).
Wells et al., *FEBS Lett.*, 23, 119-125 (1995).
Wilczek et al., *Cardiovasc. Intervent. Radiol.*, Jun. 4, 2002.
Williams et al., Biochem. J. 362:23-32 (2002).
Wong et al., *Infect. Immunity*, 67, 327-336 (1999).
Woriax et al., *Biochim. Biophys. Acta.*, 1352, 91-101 (1997).
Wu et al., *J. Biol. Chem.*, 271, 3460-3468 (1996).
Yasuda et al., *J. Cardiovasc. Pharmacol.*, 39, 784-8 (2002).
Yoon et al., *Yonsei Med. J.*, 43, 242-51 (2002).
Yoshida et al., *Biochem. Biophys. Res. Comm.*, 291, 787-794 (2002).
Zaida et al., *Free. Radic. Biol. Med.*, 27, 810 (1999).
Zhang et al., *Chines J. Path.*, 15, 518-521 (1999).

All publications, patents, and patent documents are incorporated by reference herein, as though individually incorporated by reference. The invention has been described with reference to various specific and preferred embodiments and techniques. However, it should be understood that many variations and modifications can be made while remaining within the spirit and scope of the invention.

What is claimed is:

1. A method to treat reperfusion injury brought about by myocardial ischemia in a mammal, comprising: administering to the mammal, an effective amount of sulfaphenazole wherein the administered sulfaphenazole substantially reduces the amount of infracted tissue.

2. A method to treat reperfusion injury brought about by myocardial ischemia in a mammalian donor organ, comprising: contacting the donor organ with an effective amount of sulfaphenazole, wherein the sulfaphenazole inhibits one or more cytochrome p450 enzymes, and wherein the donor organ is a heart.

3. A method to treat reperfusion injury brought about by myocardial ischemia in a mammal comprising administering to the mammal, an effective amount of sulfaphenazole suitable to substantially permit mitochondrial respiration while reducing superoxide production.

4. The method of claim 3 wherein the administered agent substantially reduces the amount of infarcted tissue.

5. The method of claim 4 wherein the administered agent reduces the amount of infarcted tissue by greater than 25%.

6. The method of claim 3 wherein the sulfaphenazole inhibits one or more cytochrome P450 enzymes.

* * * * *

UNITED STATES PATENT AND TRADEMARK OFFICE
CERTIFICATE OF CORRECTION

| | | |
|---|---|---|
| PATENT NO. | : 7,615,548 B2 | Page 1 of 5 |
| APPLICATION NO. | : 11/030717 | |
| DATED | : November 10, 2009 | |
| INVENTOR(S) | : Roberta Gottlieb | |

It is certified that error appears in the above-identified patent and that said Letters Patent is hereby corrected as shown below:

Title page, item (*) Notice: should read as follows: Subject to any disclaimer, the term of this patent is extended or adjusted under 35 U.S.C. 154(b) by 144 days.

At Page 1, Item 75, Line 5, change "Coquitlam" for David Granville to --Coquitlam, BC--.

At Page 1, Item 56, Column 1, Line 19, under Other Publications, change "1schemia" to --Ischemia--.

At Page 1, Item 56, Column 1, Line 22, under Other Publications, change "P-450" to --P450--.

At Page 1, Item 56, Column 1, Line 24, under Other Publications, change "3738," to --9738,--.

At Page 1, Item 56, Column 2, Line 4, under Other Publications, change "XP006021591," to --XP009021591,--.

At Page 1, Item 56, Column 2, Line 7, under Other Publications, change "1schemia" to --Ischemia--.

At Page 1, Item 56, Column 2, Line 37, under Other Publications, change "1schemic" to --Ischemic--.

At Page 1, Item 56, Column 2, Line 39, under Other Publications, change "Maltimore," to --Baltimore,--.

At Page 1, Item 56, Column 2, Line 48, under Other Publications, change "1schemic" to --Ischemic--.

At Page 1, Item 56, Column 2, Line 51, under Other Publications, change "1schemia" to --Ischemia--.

Signed and Sealed this

Third Day of August, 2010

David J. Kappos
*Director of the United States Patent and Trademark Office*

At Page 2, Item 56, Column 1, Line 2, under Other Publications, change "Proline Arinine" to --Proline/Arginine--.

At Column 2, Line 36, change "antifugals," to --antifungals,--.

At Column 2, Line 47, change "H+/K+-ATPase" to --$H^+/K^+$-ATPase--.

At Column 2, Line 59, change "ketaprofen." to --ketoprofen.--.

At Column 3, Line 4, change "medazapam;" to --medazepam;--.

At Column 3, Line 50, change "$O_2$*¯" to --$O_2^-$--.

At Column 4, Line 1, change "1 B" to --1B--.

At Column 4, Line 1, change " 1 B 1," to --1B1,--.

At Column 4, Line 11, change "4B 1," to --4B1,--.

At Column 4, Line 41, change "7-ethoxyresorufm;" to --7-ethoxyresorufin;--.

At Column 4, Line 51, change "antifugals;" to --antifungals;--.

At Column 4, Line 55, change "7-ethoxyresorufm;" to --7-ethoxyresorufin;--.

At Column 5, Line 8, change "H+/K+-ATPase" to --$H^+/K^+$-ATPase--.

At Column 5, Line 16, change "H+/K+-ATPase" to --$H^+/K^+$-ATPase--.

At Column 5, Line 23, change "sertraine" to --sertraline--.

At Column 5, Line 28, change "ketaprofen." to --ketoprofen.--.

At Column 6, Line 26, change "chloramphenical" to --chloramphenicol--.

At Column 6, Line 42 (Approx.), change "baulovirus" to --baculovirus--.

At Column 6, Line 67, change "methyrpone." to --metyrapone.--.

At Column 7, Line 23, change "hydroxynapthoate," to --hydroxynaphthoate,--.

At Column 7, Line 26, change "pamaote," to --pamoate,--.

At Column 7, Line 26, change "panthothenate," to --pantothenate,--.

At Column 7, Line 49, change "tartarate," to --tartrate,--.

At Column 8, Lines 9-11, after "like." delete ""Preconditioning" includes a brief period.........severe stress." and insert the same on Col. 8, Line 10, as a new paragraph.

At Column 8, Line 24, change "H+/K+ATPase" to --$H^+/K^+$ ATPase--.

At Column 8, Line 38, change "medazapam;" to --medazepam;--.

At Column 11, Line 62 (Approx.), change "derivastatin" to --cerivastatin--.

At Column 12, Lines 11-12 (Approx.), change "cardiomyocyces," to --cardiomyocytes,--.

At Column 14, Line 34, change "medazapam;" to --medazepam;--.

At Column 14, Line 42, change "mercuribenzoat," to --mercuribenzoate,--.

At Column 14, Line 52, change "H2" to --$H_2$--.

At Column 14, Line 52, change "ranifidine," to --ranitidine,--.

At Column 14, Line 61, change "medazapam;" to --medazepam;--.

At Column 15, Line 16, change "veraprimil," to --verapamil,--.

At Column 15, Lines 28-29 (Approx.), change "irebesartan;" to --irbesartan;--.

At Column 15, Lines 29-30 (Approx.), change "glyberide," to --glyburide,--.

At Column 15, Line 31 (Approx.), change "piroxican," to --piroxicam,--.

At Column 15, Line 36 (Approx.), change "probenicid," to --probenecid,--.

At Column 15, Line 41 (Approx.), change "nophenytoin(O)," to --mephenytoin(O),--.

At Column 15, Line 44, change "mocolobemide," to --moclobemide,--.

At Column 15, Line 49, change "probenicid," to --probenecid,--.

At Column 15, Line 51, change "caredilol," to --carvedilol,--.

At Column 15, Line 51, change "propafemone," to --propafenone,--.

At Column 15, Line 55, change "bufuraolol," to --bufuralol,--.

At Column 15, Lines 58-59, change "methoxyamphteamine," to --methoxyamphetamine,--.

At Column 15, Line 59, change "notriptyline," to --nortriptyline,--.

At Column 15, Line 60, change "quanoxan," to --guanoxan,--.

At Column 15, Line 62, change "celcoxib," to --celecoxib,--.

At Column 15, Line 64, change "fluxetine," to --fluoxetine,--.

At Column 15, Line 67, change "tironavir," to --ritonavir,--.

At Column 16, Line 6, change "disulfan." to --disulfane.--.

At Column 16, Line 11, change "tarolimus" to --tacrolimus--.

At Column 16, Line 13, change "cisaprine," to --cisapride,--.

CERTIFICATE OF CORRECTION (continued)
U.S. Pat. No. 7,615,548 B2

At Column 16, Line 21, change "odanstron," to --ondansetron,--.

At Column 16, Line 25, change "delaviridine," to --delavirdine,--.

At Column 16, Line 25, change "nelfmavir," to --nelfinavir,--.

At Column 16, Line 28, change "itaconazole," to --itraconazole,--.

At Column 17, Line 3, change "dyazoxide," to --diazoxide,--.

At Column 17, Line 64, change "Alzheimers" to --Alzheimer's--.

At Column 20, Line 1, change "carbo" to --carob--.

At Column 20, Lines 2-3, change "montinorillonites," to --montmorillonites,--.

At Column 21, Line 38, change "examples" to --example--.

At Column 21, Line 46, change "provides also a" to --also provides a--.

At Column 22, Line 24, change "ethylenvinyl" to --ethylenevinyl--.

At Column 24, Line 25, change "Pharmoseal" to --Pharmaseal--.

At Column 24, Line 29, change "(Wintrop)" to --(Winthrop)--.

At Column 24, Line 38, change "mercuribenzoat," to --mercuribenzoate,--.

At Column 24, Line 38, change "roliniastatin-2," to --rolliniastatin-2,--.

At Column 30, Line 15, change "EF-Tumt" to --EF-Tu$_{mt}$--.

At Column 31, Line 63, change "EF-TU$_{mt}$," to --EF-Tu$_{mt}$,--.

At Column 35, Line 44, change "IC50" to --IC$_{50}$--.

At Column 35, Line 53 (Approx.), change "InState" to --InStat--.

At Column 37, Line 16, change "a as yet" to --as a yet--.

At Column 37, Line 34, change "($^1$O$_2$*)" to --($^1$O$_2^·$)--.

At Column 37, Line 35, change "(HO$^{108}$.)." to -- (HO$^·$)--.

At Column 37, Line 49, change "epoxygnease" to --epoxygenase--.

At Column 39, Line 54, after "(2000)" insert --.--.

At Column 39, Line 64, change "407" to --407,--.

At Column 40, Line 10, change "al.,Mol." to --al., Mol.--.

At Column 40, Line 43, change "(Praha).," to --(Praha),--.

At Column 40, Line 54, change "Throughtput" to --Throughput--.

At Column 40, Line 56, change "Metab.Dispos.," to --Metab. Dispos.,--.

At Column 40, Line 63, change "Biol10," to --Biol., 10,--.

At Column 41, Line 1, change "Cardiovascl." to --Cardiovasc.--.

At Column 41, Line 12, change "Metabl." to --Metab.--.

At Column 41, Line 26, after "(1994)" insert --.--.

At Column 41, Line 29, change "Metabl." to --Metab.--.

At Column 42, Line 7, change "Chines" to --Chinese--.

At Column 42, Line 25, in claim 2, change "p450" to --P450--.